US006991818B2

(12) United States Patent
Shankaram et al.

(10) Patent No.: US 6,991,818 B2
(45) Date of Patent: Jan. 31, 2006

(54) COMPOUND ISO-SQUAMOCIN OBTAINED FROM SEEDS OF *ANNONA SQUAMOSA* AND COMPOSITION CONTAINING THE SAME

(75) Inventors: Akella Venkata Bhavani Shankaram, Hyderabad (IN); Madugula Marthanda Murthy, Hyderabad (IN); Dattatreya Manohar Akkewar, Hyderabad (IN); Mukkamala Subramanyam, Hyderabad (IN); Attaluri Narasimha Rao, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 157 days.

(21) Appl. No.: 10/107,064

(22) Filed: Mar. 28, 2002

(65) Prior Publication Data

US 2003/0050336 A1    Mar. 13, 2003

Related U.S. Application Data

(60) Provisional application No. 60/279,681, filed on Mar. 30, 2001.

(51) Int. Cl.
    A61K 35/78    (2006.01)
(52) U.S. Cl. ..................................... 424/776; 424/725
(58) Field of Classification Search ................ 424/725, 424/776
    See application file for complete search history.

(56) References Cited

U.S. PATENT DOCUMENTS

| 4,689,232 A | 8/1987 | Moeschler et al. |
| 4,721,727 A | 1/1988 | Mikolajczak et al. |
| 4,885,319 A | 12/1989 | Dougherty et al. |
| 5,229,419 A | 7/1993 | McLaughlin et al. |

FOREIGN PATENT DOCUMENTS

| CN | 1083060 | 3/1994 |
| DE | 3438763 A1 | 4/1986 |
| JP | 0912433 | 1/1997 |
| JP | 9040521 | 2/1997 |
| JP | 10101517 | 4/1998 |
| WO | WO95/19758 | 7/1995 |
| WO | WO98/49895 | 11/1998 |

OTHER PUBLICATIONS

Chopra, Y.R., "The Wealth of India, Raw Materials", Publications and Information Directorate, CSIR, I:A, Revised, p. 286, (1985).
Chopra, R.N., et al., "Glossary of Indian Medicinal Plants", CSIR, New Delhi, 20 (1956).
Harper, S.H., et al., "Annona Species as Insecticides", Ann. Appl. Biol., 104-112 (1946).
Mariappan, V., et al., "Effect of Custard-Apple Oil and Neem Oil on Survival of *Nephotettix virescens* (Homoptera: Cicadellidae) and on Rice Tungro Virus Transmission", J. Econ. Entomol., vol. 76, 573-576 (1983).
Born, L., et al., "The Relative Configuration of Acetogenins Isolated from *Annona squamosa*: Annonin 1 (Squamocin) and Annonin VI", Planta Med., 56, 312-316 (1990).**
Gypser, A., et al., "Determination of the Absolute Configuration of Annonin I, a Bioactive Natural Acetogenin from *Annona squamosa*", Tetrahedron, vol. 51, 1921-1930 (1995).
Fujimoto, Y., et al., "Squamocin, a New Cytotoxic Bis-tetrahydrofuran Containing Acetogenin from *Annona squamosa*", Chem Pharm. Bull. 36, 4802-4806 (1988).
Sahai, M., et al., "Annonaceous Acetogenins from the Seeds of *Annona squamosa*, Adjacent Bis-tetrahydrofuranic Acetogenins", Chem. Pharm. Bull., 42, 1163-1174 (1994).
Nishioka, S., et al., "Determination of Absolutes Sterochemistry at Carbinol Stereocenters of Tetrahydrofuranic Acetogenins by the Advanced Mosher Ester Method", Natural Product Letters, 5, 117-121 (1994).
Fujimoto, Y., et al., "Squamostatin-A: Unprecedented Bis-Tetrahydrofuran Acetogenin from *Annona Squamosa*", Tetrahedron Letters, 31, 533-538 (1990).
Fujimoto, Y., et al., "Annonaceous Acetogenins from the Seeds of *Annona squamosa*. Non-adjacent Bis-tetrahydrofuranic Acetogenins", Chem. Pharm. Bull. 42, 1175-1184 (1994).
Londershausen, M., et al., "Molecular Mode of Action of Annonins", Pestic. Sci., 33 427-438 (1991).
Kawazu, K., et al., "Isolation and Structure of Neoannonin, a Novel Insecticidal Compound from the Seeds of *Annona squamosa*", Agric. Biol. Chem., 53 (10), 2719-2722 (1989).
Ohsawa, K., et al., "Isolation and Insecticidal Activity of Three Acetogenins from Seeds of Pond Apple, *Annona glabra* L.", J. Pesticide Sci., 16, 93-96 (1991).
Alali, F.Q., et al., "Annonaceous Acetogenins as Natural Pesticides: Potent Toxicity Against Insecticide-Susceptible and -Resistant German Cockroaches (Dictyoptera: Blattellidae)", J. Econ. Entomol., 91 (3), 641-648 (1998).
Hui, Y.-H., et al., "Bullatacin and Bullatacinone: Two Highly Potent Bioactive Acetogenins from *Annona Bullata*", J. Nat. Prod., 52, 463-477 (1989).

(Continued)

Primary Examiner—Susan D. Coe
(74) Attorney, Agent, or Firm—DLA Piper Rudnick Gray Cary US LLP

(57) ABSTRACT

The invention relates to a novel compound isosquamocin obtained from the plant *Annona squamosa*; also provides insecticidal compositions containing isosquamocin, squamocin-B (9), squamocin-C (6), squamocin-G (2), squamocin-H (3), squamocin-J (7), squamocin-K (8), squamocin-L (5), squamocin-M (4), squamostatin-A (10), bullatalicin (11), bullatanocin (12) and three unidentified related compounds with retention times 5.88, 14.18 and 45.25 min. in HPLC obtained from the plant *Annona squamosa* and a process for the preparation of the novel compound and the insecticidal composition.

11 Claims, 6 Drawing Sheets

OTHER PUBLICATIONS

Riser, M.J., et al., "Determination of Absolute Configuration of Stereogenic Carbinol Centers in Annonaceous Acetogenins by H- and F-NMR Analysis of Mosher Ester Derivatives", J. Am. Chem. Soc., 114, 10203-10213, (1992).

Sasaki, S., et al., "In Vitro Antitumor Activities of New Synthetic Bistetrahydrofuran Derivatives as Analogs of *Annonaceous Acetogenins*", Chem. Pharm. Bull., 46 (1), 154-158 (1998).

He, K., et al., "Comparative SAR Evaluations of Annonaceous Acetogenins for Pesticidal Activity", Pestic. Sci., 49, 372-378 (1997).

Lieb, F., et al., "Annonacins and Annonastatin from *Annona squamosa*" Planta Med., 56, 317-319 (1990).

McCloud, T.G., "Annonacin, a Novel, Biolgically Active Polyketide from *Annona densicoma*", Experientia, 43, 947-949 (1987).

Araya, H., et al., "Squamosten-A, a Novel Mono-tetrahydrofuranic Acetoginin With a Double Bond in the Hydrocarbon Chain, from *Annona squamosa* L.", Chem. Pharm. Bull., 42 (2) 388-391 (1) (1994).

Ren-zhou, Y., et al., Squamosinin A: "A Novel Para-Tris-Tetrahydrofuranyl Annonaceous Acetogenins", Acta Botanica Sinica, 36 (10), 809-812 (1994).—English abstract.

Narang, C., et al., "Isolation of Acaricidal Substances Against Tropical Cattle Ticks from Sugar Apple Seeds", C.A., 119 (175835d), 282-283 (1993).

Nongluck, S., et al., "Toxicity Testing of Organic Solvent Extracts from Anona Squamosa: Effects on Rabbit Eyes and Ear Skin", C.A., 121 (294744z) (1994).

Xiangei, Z., et al., "Three Novel Chemical Compounds of Annonaceous Acetogenins from the Seeds of Annona squamosa", C.A., 123 (310315j) (1995).

Yu, J.G., et al., "Chemical Constitutents of Annona squamosa Seed", C.A., 121 (226446J( (1994).

Araya, H., et al., "Squamostanal-A, Apparently Derived from Tetrahydrofuranic Acetogenin, from *Annona squamosa*", Biosci, Biotechnol. Biochem., 58, 1146-1147 (1994).

Chao-Ming, L., et al., "Cyclopeptide from the Seeds of *Annona Squamosa*", Phytochemistry, 45, 521-523 (1997).

Saluja, A.K., et al., "Phytochemical Study of *Annona Squamosa* ", Fitoterapia, 61, 359-360 (1990).

Li, X.-H., et al., "Bullatacin, Bullatacinone, and Squamone, A New Bioactive Acetogenin, from the Bark of *Annona squamosa*", J. Nat. Prod., 53, 81-86 (1990).

Yuichi, T., "Mothproofing Agents Containing Annona Extracts, Fiber Products Treatment With Them, and Mothproofing Covers", C.A., 128 (279749f) (1998).

Bhakuni, D.S., et al., "Screening of Indian Plants for Biological Activity: Part II", Indian J. Exp. Biol., 7, 250-262 (1969).

Seetharaman, T.R., "Flavonoids from the Leaves of Annona Squamosa and Polyalthia Longifolia", C.A., 105 (149778d) (1986).

Sharma, K.R., et al., "Screening of the Compounds Isolated from the Leaves of Annona Squamosa for Anitbacterial Activity", C.A., 121 (31137w) (1994).

Rao, R. V. K., et al., "Occurrence of Kaurenoic Acid in Annona Squamosa", C.A., 107(74258) (1987).

Yang, X.J., et al., "Chemical Constituents of Annona Squamosa", C.A., 117 (86699d) (1992).

Bettarini, F., et al., "Antiparasitic Compounds from East African Plants: Isolation and Biological Activity of Anonaine, Matricarianol, Canthin-6-one and Caryophyllene Oxide", C.A., 121 (78270z) (1994).

Saxena, R.C., et al., "Larvicidal and Chemosterilant Activity of Annona Squamosa Alkaloids Against Anopheles Stephensi", C.A., 119 (175823y) (1993).

WU, Y-C., et al., "Identification of $ent$-16$\beta$, 17-Dihydroxykauran-19-oic Acid as an an Anti-HIV Principle and Isolation of the New Diterpenoids Annosquamosins A and B from *Annona squamosa*", J. Nat. Prod., 59, 635-637 (1996).

Rao, S., et al., "Fungitoxic Activity of Proanthocyanidins", C.A., 107 (4428w) (1987).

Chockalingam, S., et al., "Toxicity of Insectcides Plant Extracts and Their synergistic Effect Against Brachythemis Contaminata Fab", C.A., 117 (105987q) (1992).

Lewis, M.A., et al., "Inhibition of Respiration at Site 1 by Asimicin, an Insecticidal Acetogenin of the Pawpaw, *Asimina triloba* (Annonaceae)", Pesticide Biochem. Physiol., 45, 15-23 (1993).

* cited by examiner

(28) Squamostatin-A

(29) Reticulation-I or Neoretia

(30) Squammocin-A

(31) Squamone

(32) 2, 4 cis Trans mosinone

(33) Mosin B

(34) Molin C

(35) Annoreticuinone

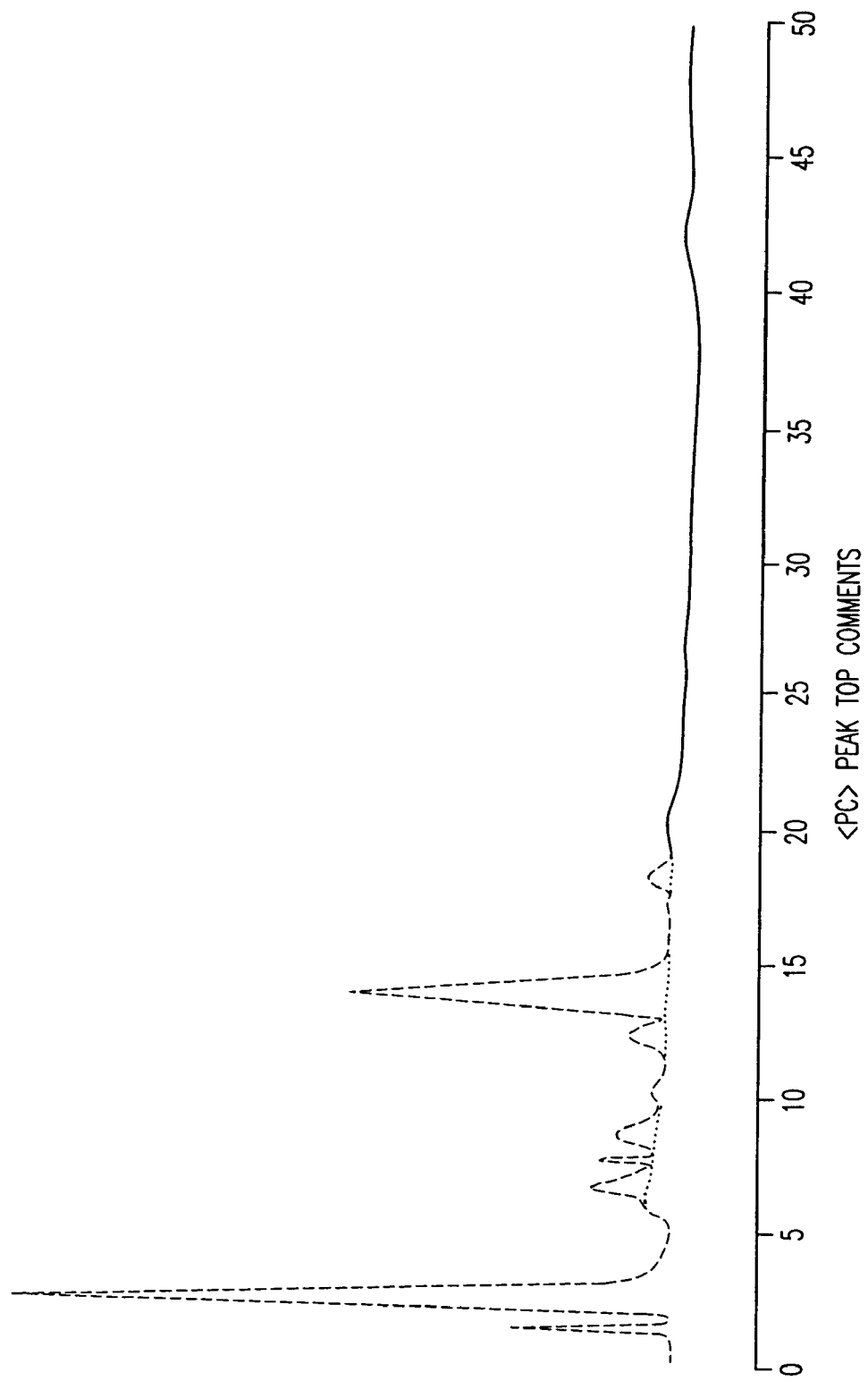

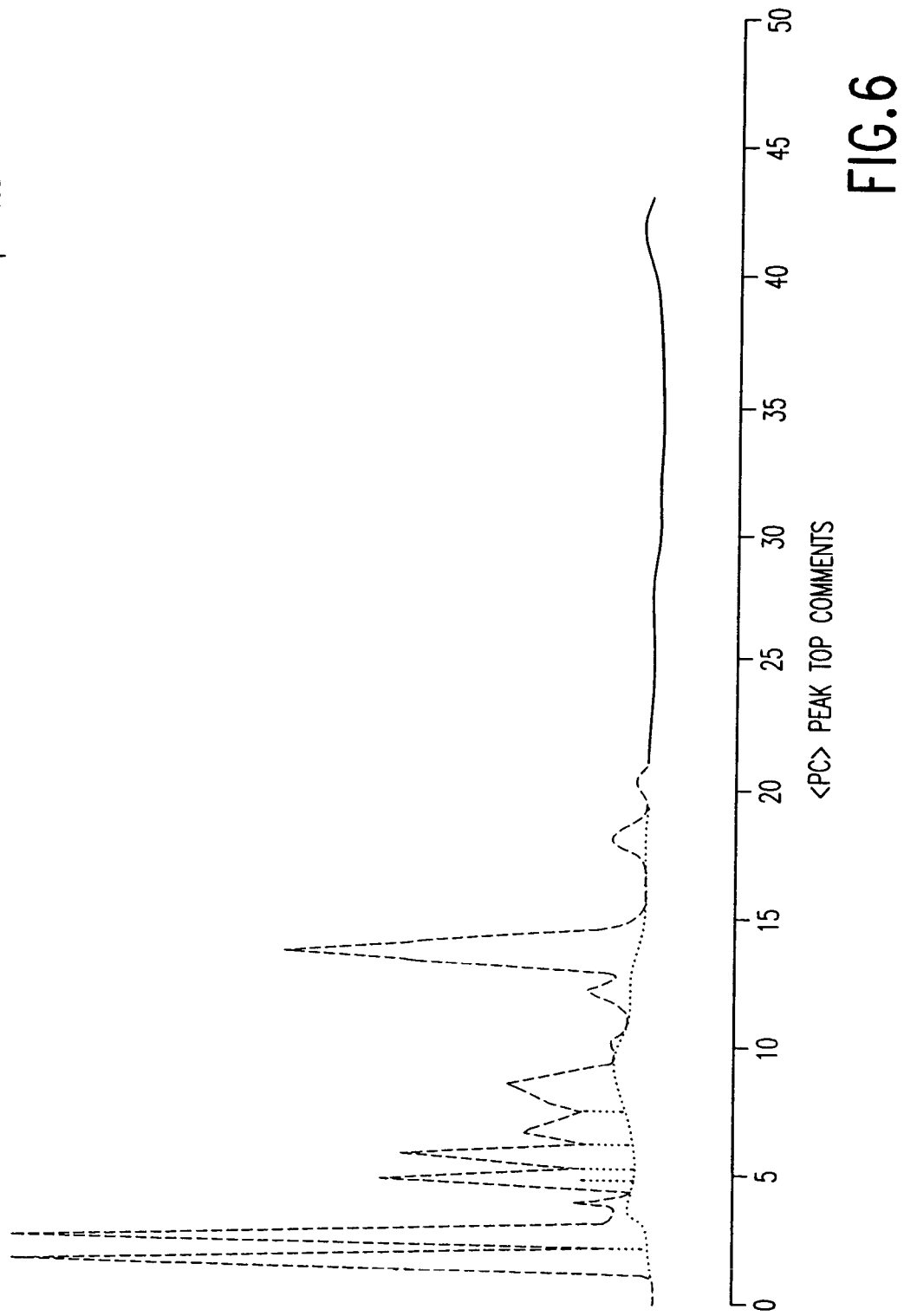

COMPOUND ISO-SQUAMOCIN OBTAINED FROM SEEDS OF *ANNONA SQUAMOSA* AND COMPOSITION CONTAINING THE SAME

BACKGROUND OF THE INVENTION

This application claims priority from U.S. Provisional Application Ser. No. 60/279,681 filed Mar. 30, 2001. The entirety of that provisional application is incorporated herein by reference.

FIELD OF THE INVENTION

The present invention relates to a novel compound designated as isosquamocin (1) and exhibiting insecticidal property. The invention also provides insecticidal composition containing isosquamocin (1), and related compounds squamocin-G (2), asimicin/squamocin-H (3); 4-deoxyasimicin/squamocin-M (4); desacetyluvaracin/squamocin L (5); motrilin/annonin-II/squamocin-C (6); neoannonin/squamocin-J (7); squamocin-K (8), squamocin-B (9), squamostatin-A (10); bullatalicin/squamostatin-B (11); bullatanocin/squamostatin-C/Annonin-V/Cherimolin-II (12) and unidentified compounds with retention times 5.88 min, 14.18 min and 45.25 min in HPLC, all obtained from the plant *Annona squamosa*. The present invention also provides methods for isolation of isosquamocin (1) and related compounds squamocin-G (2), asimicin/squamocin-H (3); 4-deoxyasimicin/squamocin-M (4); desacetyluvaracin/squamocin L (5); motrilin/annonin-II/squamocin-C (6); neoannonin/squamocin-J (7); squamocin-K (8), squamocin-B (9), squamostatin-A (10); bullatalicin/squamostatin-B (11); bullatanocin/squamostatin-C/Annonin-V/Cherimolin-II (12) and unidentified compounds with retention times 5.88 min, 14.18 min and 45.25 min in HPLC from the extract of the seeds of *Annona squamosa*. The present invention is also related to the preparation of emulsifiable concentrate formulations of the extract of seeds of *Annona squamosa* standardized and enriched with respect to isosquamocin for insecticidal applications. The composition of the extract of the seeds of *Annona squamosa* standardized with respect to isosquamocin and its formulation of the present invention are represented by the FIGS. (13) and (14) showing their analyses by HPLC. Compounds (1) to (12) described in the present invention were characterized by their physical data, optical rotation, CD spectra, $^1$HNMR spectra, $^{13}$CNMR spectra and mass spectra.

BACKGROUND OF THE TECHNOLOGY

*Annona squamosa* (Custard apple; Telugu: Sitaphal) is a small tree and it is found in the hilly tracts and waste lands of several regions of India. It is also cultivated for its delicious fruits and the annual production of fruits was estimated to be 12,000 tones in Andhra Pradesh, India. The seeds were reported to possess insecticidal and pesticidal properties. The leaf was also reported to possess insecticidal, stimulant, antispasmodic, sudorific and anthelmintic properties. (The Wealth of India, Raw Materials, IA, revised publication, Y. R. Chopra, Ed., p. 286, Publication and Information Directorate, CSIR, New Delhi, 1985; Glossary of *Indian Medicinal Plants*, R. N. Chopra, p. 20, CSIR, New Delhi, 1956). A resinous concentrate prepared by the solvent extraction of the seeds of *Annona squamosa* was found to be a contact insecticide against *Aphis phabae, Macrosiphoniella sanbornii* and the toxicity was of the same order as rotenone (S. H. Harper, C. Potter and E. M. Gillham, *Ann. Appl. Biol.*, 34, 104, 1947). Solvent extracts of the seeds of *Annona squamosa* were found to be toxic to stored grain pests (*Indian J. Exptl. Biol.* 2, 519, 1971). The petroleum ether insoluble part of the seed oil of *Annona squamosa* was found to be toxic to mosquito larvae *Culex fatigans* Wied (P. Cheema, R. S. Dixit, T. Koshi and S. L. Perti, *J. Sci. Ind. Res.* 17C 132, 1958). The ethanolic extract of the plant *Annona squamosa* excluding the root caused mortality to the insects *Musca domestica*, (63%) and *Tribolium castaneum*, (43%) (C. K. Atal, J. B. Srivasthava, B. N. Dhawan, *J. Exptl. Biol.* 16, 330) An oily fraction prepared by the solvent extraction of the seeds of *Annona squamosa* was emulsified in water with a detergent and the emulsion reduced the mortality of the leaf hopper of rice *Nephotettix virescens* (distant) and its transmission of the Rice Tungro virus (V. Mariappan and R. C. Saxena, *J. Econ. Entomol.* 76, 573, 1982). German Patent DE 3,438,763 and the U.S. Pat. No. 4,689,232 claimed the isolation and insecticidal activity of an unidentified organic compound designated as annonin-I from the seeds of *Annona squamosa*. Subsequently, annonin-I was shown to possess the molecular structure shown in the diagram L. Born, F. Lieb, J. P. Lorentzen, H. Moeschler, N. Nonfon, R. Solner and D. Wendisch, *Planta Medica* 56, 312, 1990; A. Gypser, C. Bulow and H. D. Scharf, *Tetrahedron*, 51, 1921, 1995) and it was considered to be identical with squamocin isolated from the seeds of *Annona squamosa* (Y. Fujimoto, T. Eguchi, K. Kakinuma, N. Ikekawa, M. Sahai and Y. K. Guptha, *Chem. Pharm. Bull*, 36, 4802, 1988; M. Sahai, S. Singh, M. Singh, Y. K. Guptha, S. Akashi, H. Araya, W. Hara, T. Eguchi, K. Kakinuma and Y. Fujimoto, *Chem. Pharm. Bull.*, 42, 1163, 1994; H. Araya, C. Murasaki, M. Sahai and Y. Fujimoto, *Natural Product Letters*, 5, 117, 1994). Analogues of squamocin designated as squamocin-B (9), squamocin-C/motrilin (6), squamocin-D/asiminacin (16), squamocin-E (17), squamocin F (18), squamocin-G (2), squamocin-H/asimicin (3), squamocin-I (19), squamocin-J/neoannonin (7), squamocin-K (8), squamocin-L (5), squamocin-M (4), squamocin-N (20) (M. Sahai, S. Singh, M. Singh, Y. K. Guptha, S. Akashi, R. Yujii, S. Singh, K. Hirayama, M. Asaki, H. Araya, N. Hara, T. Eguchi, K. Kakinuma and Y. Fujimoto, *Chem. Pharm. Bull*, 42, 1163, 1994) and squamostatin-A/annonin XVI/almunequin (10,) Y. Fujimoto, C. Murasaki, K. Kakinuma, T. Eguchi, N. Ikekawa, M. Furugya, K. Hirayama, T. Ikekawa, M. Sahai, Y. K. Guptha and A. B. Ray, *Tetrahedron Lett.* 31, 535 (1990) squamostatin-B/Annonin VIII/bullatalicin (11), squamostatin-C/bullatanocin (12), squamostatin-D (21) and squamostatin-E (22) (Y. Fujimoto, C. Murasaki, H. Shimada, S. Nishioka, K. Kakinuma, S. Singh, M. Singh, Y. K. Guptha and M. Sahai, *Chem. Pharm. Bull.* 42, 1175, 1994) were also isolated from the seeds of *Annona squamosa*. Annonin-I/squamocin (15), annonin III/squamocin-C/motrilin (6) and annonin VI (assumed to have structure 2) having three hydroxyl groups and molecular formula $C_{37}H_{67}O_7$ were reported to possess a high degree of insecticidal activity. The activity decreased in the order 1>6>Annonin v1 and the mechanism of action involved the. Inhibition of mitochondrial respiration and the primary target was considered to be the enzyme NADH-cytochrome C-reductase (M. Londerhausen, W. Leicht, F. Lieb, H. Moeschler and H. Weiss, *Pesticide Science* 33, 427, 1991). A compound considered to be identical with squamocin (15) along with a compound designated as neoannonin (molecular formula, $C_{35}H_{62}O_6$; 7) were isolated from the seeds of *Annona squamosa* and both were found to have insecticidal activity against the fruitfly *Drosophila melanogaster*. The $^1$H and $^{13}$C NMR spectra of squamocin of this investigation and squamocin (15) reported earlier appeared to be identical, the optical rotations of squamocin of this investigation $[\alpha]_D^{22}$+14.9 (C=0.94, MeOH) is different from squamocin (15) $[\alpha]_D$+1.5 (c=1.7, MeOH) referred to earlier. Thus, squamocin obtained in this investigation and squamocin (15) referred to earlier appear to be not identical. Neoannonin was considered to be identical with squamocin-J (7) discussed earlier (K. Kawazu, J. P. Alcantara and A. Kobayashi, *Agric Biol. Chem.*, 53, 2719, 1989). Similar discrepancies in the optical rotations of squamocin have also been subsequently reported.

The insecticidal activity of squamocin (15) was compared with that of asimicin/squamocin-H (3), molecular formula, $C_{37}H_{67}O_7$ and desacetyluvaricin/squamocin-L (5), molecular formula, $C_{37}H_{66}O_6$, isolated from the ether extract of seeds of *Annona glabra* L. against the insect pest *Callosobruchus chinensis* by topical application and asimicin (3) was the most potent followed by (15) and (5). (15), and the ether extract were also found to have lethal insect antifeedant and growth inhibitory properties on various insect pests of agricultural importance belonging to the orders, Lepidoptera, Coleoptera and Hemiptera (K. Ohsawa, A. Atsuzawa, T. Mitsui and I, Yamomota, *J. Pesticide Sci.,* 16, 93 (1991).

U.S. Pat. Nos. 8,60,531 and 4,885,319 claimed the isolation of pure asimicin (3) from the fruits of *Rollina sylvatica* and the bark of *Asimina triloba* also belonging to the family Annonaceae and its potential for the control of insect pests, mosquito larvae, spider mites, aphids, mexican bean beatle, striped cucumber beatle, blowfly larvae, arthropods and nematodes.

U.S. Pat. No. 4,721,727 claimed pure asimicin (3) or a component of the plant extract belonging to the family Annonaceae and a wide range of compounds fitting into the general formula as insecticides Asimicin (3) and parviflorin, molecular formula, $C_{35}H_{62}O_7$ presumably identical with squamocin-E (17) and related compounds and some organic synthetic insecticides were found to be lethal to susceptible and insecticide resistant German cockroach *Blattella germanica* (L) and asimicin was more active than parviflorin/squamocin E (17) (F. Q. Alali, W. Kaakeh, G. W. Bennett and J. L. McLaughlin, *J. Econ. Entomol.* 91, 641, 1998).

Squamocin-G was considered to be identical with bullatacin isolated from *Annona bullata* (Y.-H. Hul, J. K. Rupprecht, Y-H. Liu, J. E. Anderson, D. L. Smith, C-J. Chang, and J. L. Mc Laughlin, *J. Nat. Prod.* 52, 463, 1989 and U.S. Pat. No. 5,229,419. The molecular structure of bullatacin has since been revised as (2) (M. J. Rieser, Yu-hua Hui, J. K. Rupprecht, J. F. Kozolowski, K. V. Wood, J. L. McLaughlin, P. R. Hanson, Z. Zhuang and T. R. Hoye, *J. Am. Chem. Soc.* 114, 10203, 1992). The $^{13}C$ NMR spectrum of squamocin G (2) showed signals at δ, 24.4 PPM and 25.7 PPM which were absent in the $^{13}C$ NMR spectrum of bullatacin. This observation clearly points out that squamocin G and bullatacin are isomeric compounds. A compound with structure and stereochemistry as shown in FIG. 1 was synthesized and the $^{13}C$ NMR spectra of squamocin G (2) and the synthetic compound were identical. The structure of bullatacin therefore requires revision. U.S. Pat. No. 5,229,419 claims the isolation of bullatacin from the bark of *Annona bullata* and its potential as an insecticide for the pests of importance in agriculture and public health such as blowfly larvae toxicity, southern corn rootworm (24 ppm), two sported spider mite (10 ppm) and cotton aphid (1 ppm) and for the treatment of cancer. It was also claimed that partially purified crude extracts of bark of *Annona bullata* as an insecticide.

Squamocin-G and its isomer squamocin-H (asimicin) were reported to have cytotoxic activity against P-388 mouse leukemia, PC-6, lung human cancer and NUGC-3 human cancer cell lines (S. Sasaki, K. Maruta, H. Naito, R. Maemura, E. Kawahara and M. Maeda, *Chem. Pharm. Bull.* 46, 154, 1998).

Asimicin/squamocin-H (3), motrlin/squamocin-C/Annonin III (6) and a related compound trilobin (24) which possess an adjacent bis tetrahydrofuran moiety also showed highly potent insecticidal activity against the yellow fever mosquito *Aedes aegyptii*. The insecticidal activity of asimicin (3 LC 50, 2.7 mg/lit$^{-1}$) is superior to that of bullatalicin/squamostatin-B (11, LC 50, 9 mg/lit$^{-1}$) and annonacin A (25) (LC 50, 10.8 mg/lit$^{-1}$) which posses a structurally different nonadjacent bis tetrahydrofuran moiety and a single tetrahydrofuran ring respectively (K. He, L. Zeng, Q. Ye, G. Shi, N. H. Oberlies, G-Xian Zhao, C. J. Nzoku and J. L. Mc Laughlin, *Pestic. Sci.* 49, 372, 1997).

The seeds of *Annona squamosa* also yielded monotetrahydrofuran derivatives annonacin (26), annonacin A (25) (F. Lieb, M. Nonfon V. W. Neumann and D. Wendisch, *Planta Medica,* 56, 317, 1990) and annonastatin (27) (G. Mc Cloud, D. L. Smith, Ch. J. Chang and J. M. Cassady, *Experientia* 43, 947, 1987) and they were found to be toxic to the nematode *Caenohabditis elegans* and the insect *Phaedon cochleariae*, Chinese Patent CN 1,083,060 claimed annonaceous acetogenins having a single tetra hydrofuran ring and adjacent bis tetrahydrofuran moiety isolated from the seeds of *Annona sugmosa* and *Goniothalamus howii* Merr et. Chun as insecticides Squamostene-A (28) (C. H. Araya, N. Hara, Y. Fujimoto and M. Sahai, *Chem. Pharm. Bull.* 42, 388, 1994), reticulacin-1(29) C. C. V. Zheng, R. Z. Yang, G. W. Qin, R. S. Yu and D. J. Fan (*Acta Botanica Sinica* 36, 809, 1994) isolated from the seeds of *Annona squamosa* also possess a single tetrahydrofuran ring.

Japanese Patent JP 10,101,517 described the moth proofing agents for fiber products containing ether extracts of seeds of *Annona squamosa*, which controlled the larvae of *Tinia pellionella* and *Antherenus nerbasci*. PCT International Patent Application WO 9,519,758 and JP 0,940,521 claimed preparations containing bis tetrahydrofuran group and monotetrahydrofuran group respectively for hair growth promotion and hair loss prevention. JP 0,912,433 described antidandruff, anti-itching and hair loss preventing preparations containing fat-soluble fractions of seeds of *Annona squamosa*.

Patent application WO 9,849,895 described the isolation of three compounds having one tetrahydrofuran ring exhibiting selective cytotoxic activity against certain specific human tumor cells from the bark of *Annona squamosa*.

A compound possessing the same molecular weight and fragmentation pattern in its mass spectrum resembling squamocin was found to be an acaricide against tropical cattle ticks (C. Narang, M. Sugunya, R. Chainarong, J. Suratwadee and J. Weerapool, *C.A.* 119:175835d). Organic solvent extracts of seeds of *Annona squamosa* were found to be useful for the management human lice and ethonolic extract of leaves and seeds showed mildest toxicity to rabbit eyes and no toxicity to ear skin (S. Nongluck; G. Wandee; S. Aim-on; L. Khanong; T. Pongkrit; *C.A* 121:294744z. Three compounds designated as neodesacetyluvaricin, neoannonin-B and neoreticulatacin (Z. Xiangei, Y. Renzhow, Q. Guiwei, X. Rensheng and F. Danjun, *C.A.* 123, 310,315j) annonin, daucosterol desacetyluvaricin and squamostatin-B (G. Yu, X. Z. Luo, C. Y. Lin, L. Sun, S. L. Hong and L. B. Ma, *C.A.* 121, 2,264,46d), squamostanol-A (H. Araya, N.

Hara, Y. Fujimoto and M. Sahai, *Biosci, Biotechnol. Biochem,* 58, 1146, 1994) and an acetogenin having a tristetrahydrofuran skeleton designated squamosinin-A (30) (R. Z. Yang, X-C. Zheng, G.-W. Quin and R.-S. Xu, *Acta Botanica Sinica,* 36, 809, 1994, C.A. 124, 170607z) were also reported from the seeds of *Annona squamosa*. Cyclopeptide derivatives were also isolated from the seeds of *Annona squamosa* (Lichao-Mang, T. Ning-Hua, M U. Quing. Z. uilan, Hao Xiao-Jiang, Wuyu and Z. Jun *Phytochemistry,* 45,5 21, 1997). A saponin stigmasta-5, 24 (28)-diene-3β-ol-α-L=rhamnoside was also isolated from the seeds of *Annona squamosa* (A. K. Saluja, D. D. Santani, *Fitoterapia* 61, 359, 1990. *C.A:* 114,139811f)

Investigation of the stem bark of *Annona squamosa* yielded bullatacin, bullatacinone and squamone (31) having an adjacent bis tetrahydrofuran moiety (X. H. Li, Y. H. Hui, J. K. Rupprecht, Y. H. Liu, K. V. Wood, D. L. Smith, C. J. Chang and J. L. Mc Laughlin, *J. Nat. Prod.* 53, 81, 1990) and the monotetra-hydrofuran derivatives 2,4-(cis and trans)-mosinone-A (32), mosin-B (33), mosin-C (34) and annoreticulone (35) possessing selective cytotoxic activities against some human tumor cell lines (PCT. Int. WO 98,49, 895; T. Yuichi C. A. 128; 279749 f).

The ethanolic extract of leaves and stem of *Annona squamosa* was found to possess anticancer activity. (D. S. Bhakuni, M. L. Dhar, M. M. Dhar, B. N. Dawan and B. N. Mehrotra, *Indian J. Exptl. Biol.,* 250, 1969). Chemical investigation of the leaves resulted in the isolation of a mixture of aliphatic alcohols, a mixture of β-sitosterol, stigmasterol camposterol (T. R. Seetharaman C.A. 105, 149778 d), 16-hentria contanone sitosterol and stigmasterol showing antibacterial activity and hexacosanol, octacosanol and triacontanol (K. Rajesh Sharma and M. Behari, *C.A.* 121: 31137w) and the flavonoids quercentin-3-0-rutinoside and quercentin-3-B-galactoside (T. R. Seetharaman, *C.A.* 105:149778d) (R. V. K. Rao and T. Satyanarayana, *C.A.* 107 74258q). The branches of *Annona squamosa* gave the alkaloids squamosamide, liriodenine moupinamide, annonaine, sachanoic acid and diterpenoids belonging to the kaurane group (X. J. Yang, L. Z. Xu, N. J. Sun, S. C. Wang and Q. T. Zheng, *Yaoxue Xue, Buo,* 27, 185, 1992, *C.A.* 117, 86699d) and annonaine was found to possess antifungal activity (F. Bettarani, G. E. Borganvi, T. Fiorini, K. Gjagaliaridi, V. Caprioli, P. Massardo and S. A. Donegani, *C.A.* 121:78270z). Alkaloids isolated from *Annona squamosa* were also found to possess larvicidal and insect growth regulating and chemosterilant activities against the mosquito Anopheles stephensi at 50–200 ppm. Mortality in the larvae, pupae and adults was 52–92% (R. C. Saxena, V. Harshan, A. Saxena, P. Sukumaran, M. C. Sharma and M. Lakshmana Kumar, *C.A.* 119:175823 y).

Phytochemical analysis of fruits of *Annona squamosa* also resulted in the isolation of alkaloids and several diterpenoids of kaurane group of which 16β, 17-dihydroxy-ent-kauran-19-oic acid showed significant activity against HIV replication in H9 lymphocyte cells (Y. C. Wu, Y-C. Hung, F. R. Chang, M. Cosentino, H. K. Wang and K. H. Lee, *J. Nat. Prod.* 59, 635, 1996). The fruits were also found to contain procyanidin, which was toxic to the fungal pest *Rhizoctonia solani* (S. Seetharama Rao and K. V. N. Rao, *C.A.* 107: 4428 h)

Extracts of *Annona squamosa* were toxic to the dragonfly nymph *Brachythemis contaminata* Fab and they were also found to have synergistic effect with the insecticide fenthion (S. Chockalingam, A. Kuppusamy, G. Punithaavathy and T. Manoharan *C.A.* 117:105987q).

The insecticidal and cytotoxic activities of the organic solvent extracts of the seeds of *Annona squamosa* have been correlated with the compounds having adjacent bis tetrahydrofuran moiety (A) nonadjacent bis tetrahydrofuran moiety (N) and single tetrahydrofuran rings (S) and the activities of group (A) are superior to those of groups (N) and (S). Common structural features of all the active compounds would be (they usually contain 35 or 37 carbon atoms,) three to six hydroxyl groups, α,β-unsaturated γ-lactone moiety substituted with a methyl group and a vacant olefinic position. Highly potent analogues in group (A) invariably contain two hydroxyl groups flanking the tetrahydrofuran ring (C-15 and C-24 for C-37 class and C-13 and C-22 for C-35 class and highest activity is noticed with compounds having a third hydroxyl group located at C-4 (asimicin squamocin-G and squamocin-E) C-28 (squamocin/annonin-I), C-29 (motrilin/suqamocin C) and at C-26 for squamocin-B. The insecticidal activity of these compounds was correlated with the inhibition of mitochondrial respiration leading to the decrease in concentration of ATP and finally lethality due to deprivation of metabolic energy and the enzyme cytochrome C-reductase was the primary target (M. Londerhausen, W. Leicht, F. Lieb and H. Moeschler, *Pesticide Science,* 33, 421, 1991; M. A. Lewis, J. T. Aranson, B. J. Philogene, J. K. Rupprocht and J. L. Mc Laughlin, *Pesticide Biochem. Physiol.* 45, 15, 1993). The anticancer activity of these compounds was also correlated with the selective inhibition of cancerous cells by the blockage of monochondrial complex I (NADH-ubiquinone oxido reductase) an essential enzyme in complex 1 of electron transport system and inhibition of plasma membrane NADH oxidase depleting ATP and inducting apoptosis (programmed cell death) in malignant cells (A. Evans and V. C. Murthi, *Tetrahedrdron Letters* and references cited therein). Thus, it is known from the prior art, that (1), organic solvent extracts of seeds of *Annona squamosa* possess potent insecticidal properties; (2), the organic solvent extracts yielded a very potent insecticide designated annonin I/squamocin; (3), the organic solvent extracts of seeds of *Annona squamosa* gave at least fourteen analogues of squamocin designated squamocin B to squamocin N, squamostatin A, squamostatin B, squamostatin C and squamostatin D and squamostatin E and of these squamocin H, squamocin J, squamocin L and squamostatin B/bullatalicin(11); showed insecticidal activity and (4) the remaining compounds are also expected to have a similar insecticidal activity. It is also known from the prior art, that several analogues of Annonin-I/squamocin having a methyl substituted γ-lactone with a vacant olefinic position and an adjacent bistetrahydrofuran moiety, or a single tetrahydrofuran ring and a number of hydroxyl groups are potential candidates as insecticides.

SUMMARY OF THE INVENTION

One advantage of the invention is to provide a novel compound isosquamocin exhibiting insecticidal property.

Another advantage of the invention is to provide insecticidal compositions containing isosquamocin, squamocin-B (9), squamocin-C (6), squamocin-G (2), squamocin-H (3), squamocin-J (7), squamocin-K (8), squamocin-L (5), squamocin-M (4), squamostatin-A (10), bullatalicin (11), bullatanocin (12) and three unidentified related compounds with retention times 5.88, 14.18 and 45.25 min. in HPLC.

Yet another advantage of the invention is to provide a process for the preparation of pure samples of isosquamocin, squamocin-B, squamocin-C, squamocin-G, squamocin-J, squamocin-H, squamocin-K, squamocin-L, squamocin-M, squamostatin-A, bullatalcin, bullatanocin and three unidentified analogues with retention times 5.88, 14.18 and 45.15 min. in HPLC.

Still another advantage is to evaluate the biological activity of the compounds of the invention.

Another object is to provide novel insecticidal compositions containing the novel compounds identified from the plant *Annona squamosa*.

The invention provides a novel compound isosquamocin obtained from the plant *Annona squamosa*. The invention also provides insecticidal compositions containing isosquamocin, squamocin-B (9), squamocin-C (6), squamocin-G (2), squamocin-H (3), squamocin-J (7), squamocin-K (8), squamocin-L (5), squamocin-M (4), squamostatin-A (10), bullatalicin (11), bullatanocin (12) and three unidentified related compounds with retention times 5.88, 14.18 and 45.25 min. in HPLC obtained from the plant *Annona squamosa*. The invention also provides process for the preparation of the novel compound and the insecticidal composition.

Additional advantages and novel features of the invention will be set forth in part in the description that follows, and in part will become more apparent to those skilled in the art upon examination of the following or upon learning by practice of the invention.

BRIEF DESCRIPTION OF THE FIGURES

In the drawings:

FIG. 5 represents HPLC of the standardized extract of the seeds of *Annona squamosa*; and FIG. 6 represents HPLC of the formulation of standardized extract of the seeds of *Annona squamosa*.

DETAILED DESCRIPTION OF THE INVENTION

Figure 1:
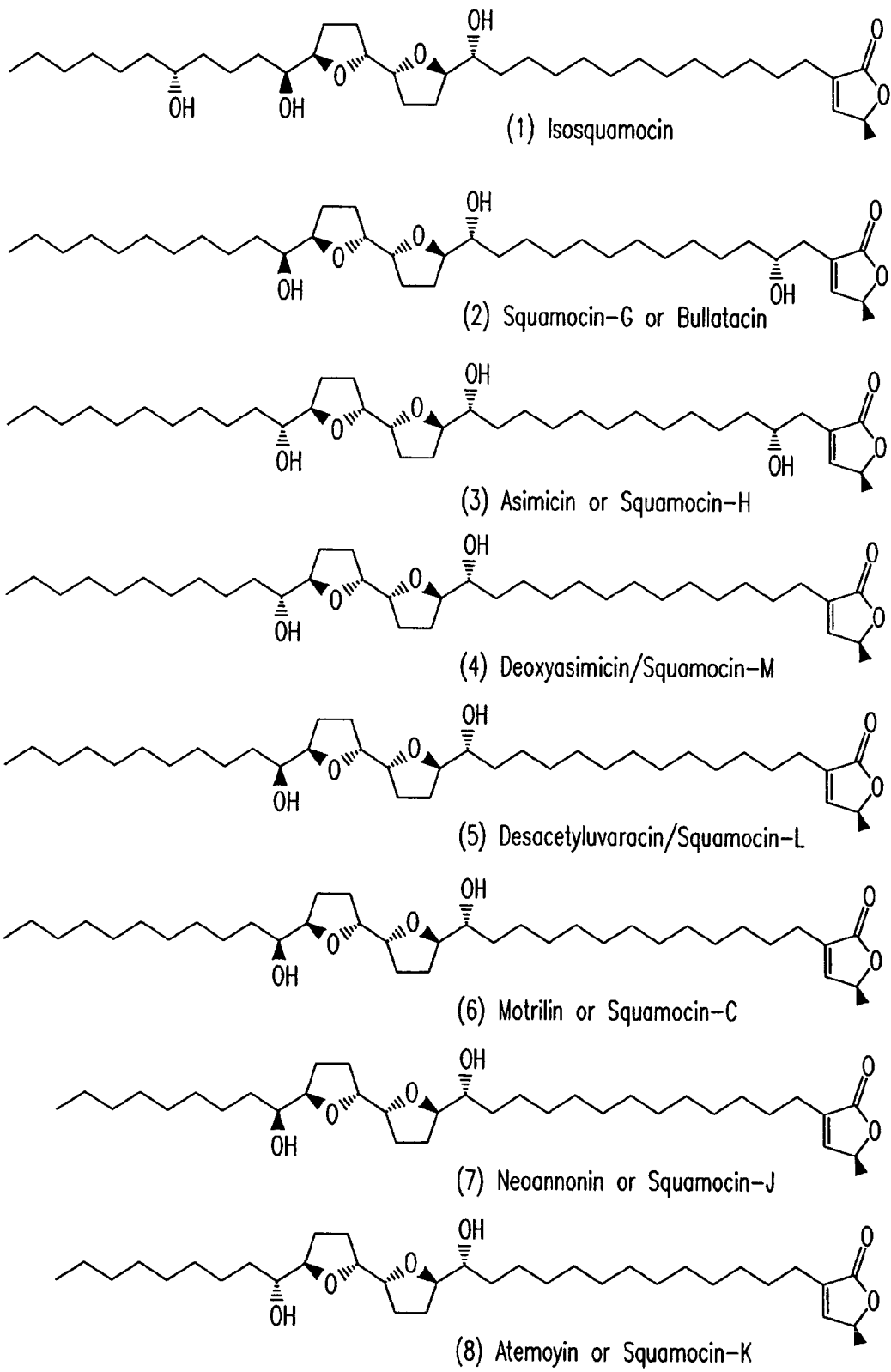
FIG. 1 represents structures of compound (1) to (8)
Figure 2:
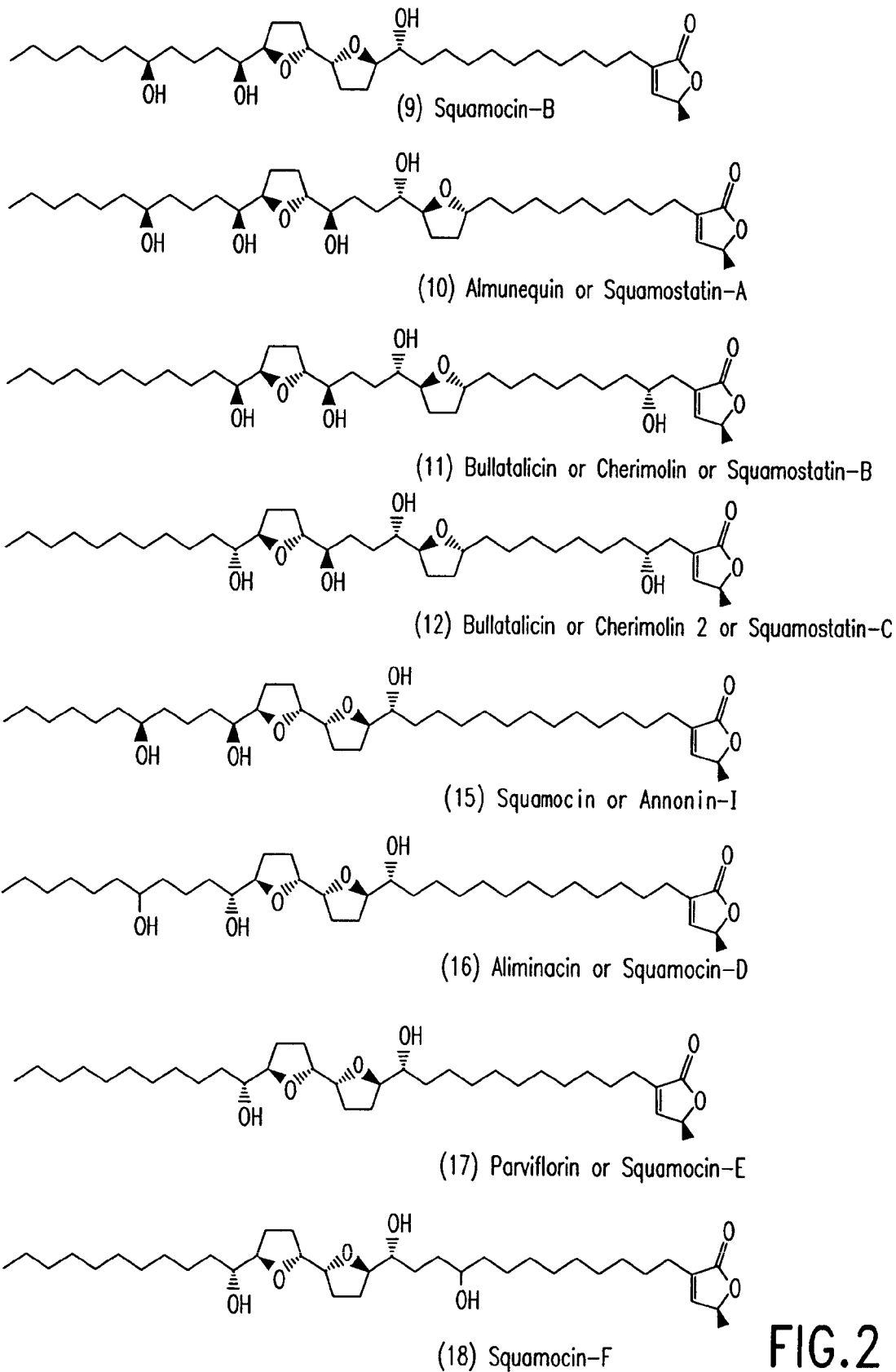
FIG. 2 represents structures of compound (9) to (18) except (13 and 14)
Figure 3:
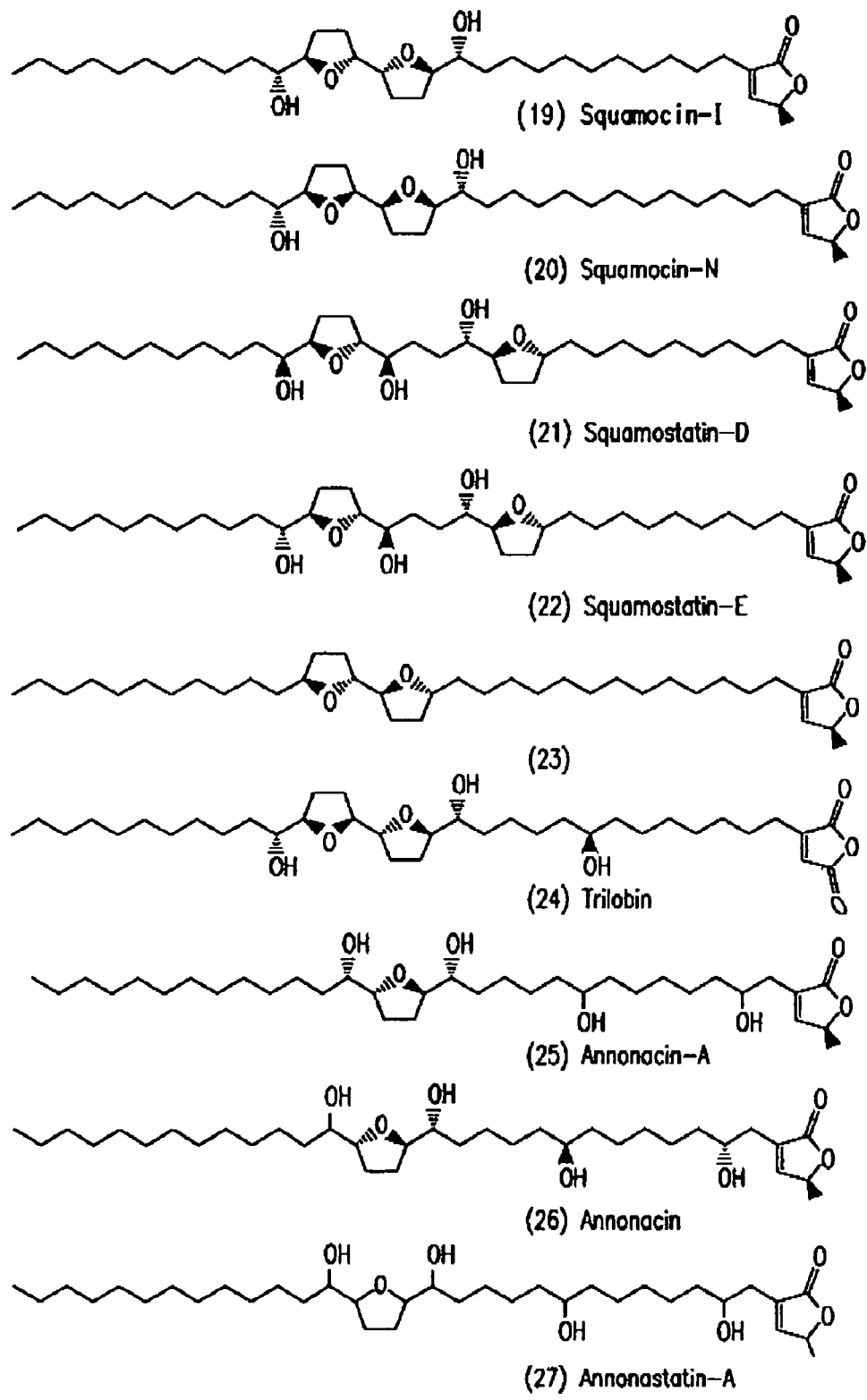
FIG. 3 represents structures of compound (19) to (27)
Figure 4:
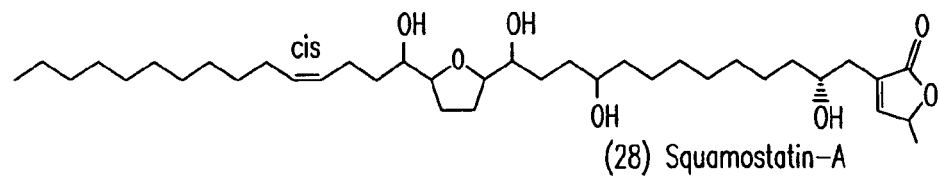
FIG. 4 represents structures of compound (28) to (35)
Figure 4:
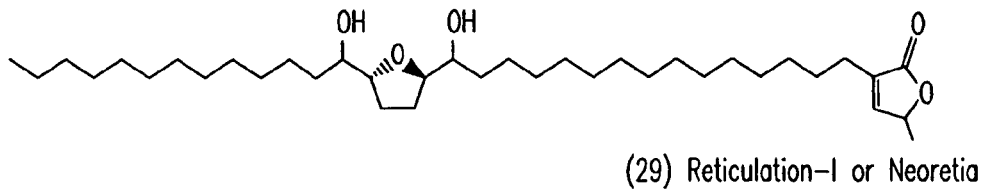
Figure 4:
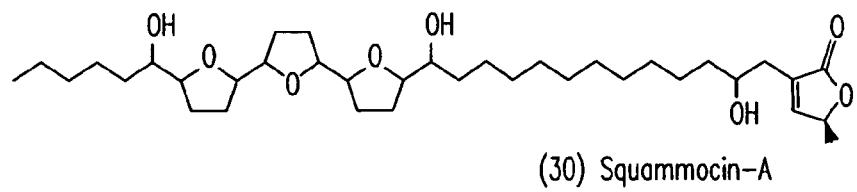
Figure 4:
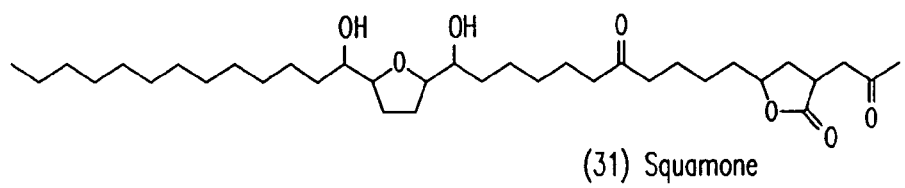
Figure 4:
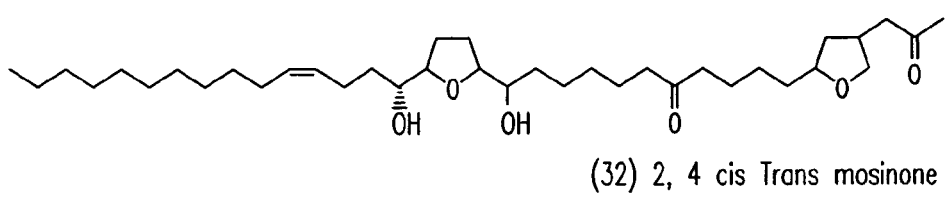
Figure 4:
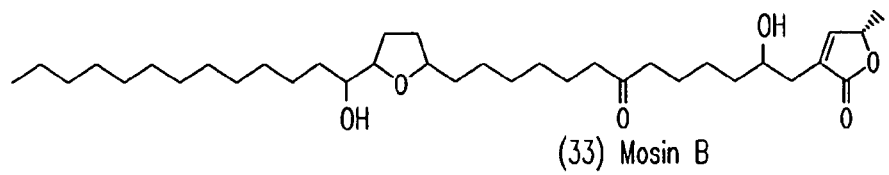
Figure 4:
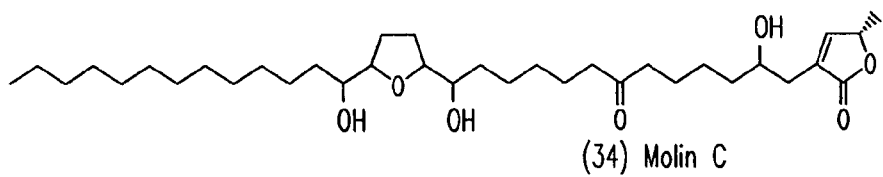
Figure 4:
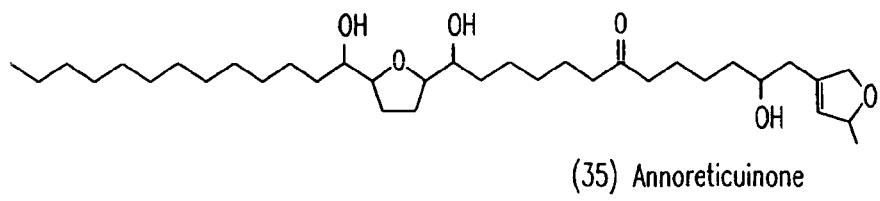

Accordingly, the present invention provides a novel insectcidal compound called isosquamocin represented by the structural formula, isolated from the plant *Annona squamosa*. The invention also provides insecticidal compositions containing isosquamocin, squamocin-B (9), squamocin-C (6), squamocin-G (2), squamocin-H (3), squamocin-J (7), squamocin-K (8), squamocin-L (5), squamocin-M (4), squamostatin-A (10), bullatalicin (11), bullatanocin (12) and three unidentified related compounds with retention times 5.88, 14.18 and 45.25 min. in HPLC.

The invention also provides process for the preparation of the insecticidal composition composed of the above mentioned 15 compounds and its formulation and it is carried out in the following manner according to the process of the present invention.

One more embodiment of the invention relates to a stable emulsifiable concentrate of acetogenin as an Insecticidal composition comprising essentially an effective amount of compound isosquamocin (1), and containing optionally one or more related compounds selected from group consisting of squamocin-G (2), asimicin/squamocin-H (3); 4-deoxyasimicin/squamocin-M (4); desacetyluvaracin/squamocin L (5); motrilin/annonin-II/squamocin-C (6); neoannonin/squamocin-J (7); squamocin-K (8), squamocin-B (9), squamostatin-A (10); bullatalicin/squamostatin-B(11); bullatanocin/squamostatin-C/Annonin-V/Cherimolin-II (12) and unidentified compounds with retention times 5.88 min, 14.18 min and 45.25 min in HPLC, all derived from the plant *Annona squamosa* along with additives or carriers.

Another embodiment of the invention, the additives used for preparing incectcidal compositions are selected from emulsifiers, solvents and/or any other conventional ingredients suitable for preparing an emulsion. Still another embodiment of the invention, the concentration of acetogenins in the final composition is in the range of 2 to 10%.

In still another embodiment, said composition is effective to act against insects selected from group consisting of variegated cutworm, black wire weevils, first and third instar larvae of origental armyworm *Mythimna aeperata* WLK, Southern Corn rootworm, spotted spidermite, green peacg aphid (GPA) and Corn plant hopper (GPH). One more embodiment of the invention relates to a process for the preparation of an extract of seeds of *Anona squamosa* standardized with respect to a novel active insecticidal compound designated as Isoquamocin and related compounds from the seeds of *Anona squamosa* known as custard apple which comprises of:

(a) disintegrating the custard apple seeds into powder, (b) subjecting the said powder of step (a) to continuous extraction using methanol or aqueous methanol, ethanol or aqueous ethanol at an ambient temperature, (c) concentrating the extract of step (b) and stirring the concentrate with petroleum ether/hexane having boiling point in the range of 60–80° C. and phased separately by conventional methods.

(d) stirring the heavy phase of step (c) containing the active ingredient Isoquamocin, squamocin G, squamocin H, squamocin M, squamocin L, squamocin C, squamocin J, squamocin K, squamocin B, squamostatin A, squamostatin B, squamostatin C and the unidentified compounds with retention times 5.88, 14.18 and 45.25 minutes with suitable organic solvent and water as required and separating the phase by conventional methods, (e) concentrating the organic phase of step (d) to yield standardized extract of *Anona squamosa* (SESAS) in the form of brown semisolid, (f) dissolving the semisolid from step (e) in an organic solvent and subjecting to column chromatography over silica gel using eluants of increasing polarity selected from petroleum ether/hexane, mixture of ethyl acetate/hexane in the ratio 9/1, 8/2, 7/3, 6/4, 5/5, 4/6, 3/7, 2/8 and 1/9 and ethyl acetate as eluant leading to solid and semisolid residue, and (g) finally dissolving the residue obtained from (f) subjecting it to HPLC (RP-18 column), mobile phase (methanol/water) leading pure compounds claimed in claim 6, step (d) having purity of 90–95%

An embodiment of the present invention relates to a process, wherein the disintegration of seeds in step (a), is carried out in a mill.

In still another embodiment of the invention relates to a process, wherein the disintegrated seeds powder obtained in step (b), is having particle size in the range of British Standard Sieves BSS-7 (0.2 mm) to BSS-72 (2.4 mm).

In still another embodiment of the invention, the solvents used in step (b) for extracting disintegrated seeds is selected from methanol, aqueous methanol, ethanol, aqueous ethanol and most preferably methanol.

In yet another embodiment, the methanol extract obtained in step (c) is concentrated at atmospheric pressure or under reduced pressure.

In yet another embodiment of the invention, the organic solvent used in step (d) for selective separation of active compounds is selected from benzene, 2-butanone, chloroform, dichloromethane, dichloroethane, diethyl ether, disopropyl ether, ethyl acetate, MTB, toluene and most preferably ethyl acetate.

In yet another embodiment of the invention, the ethyl acetate extract obtained in step (e) is concentrated at atmospheric pressure or under reduced pressure. Yet another embodiment of the invention, the concentrated extract obtained in step (e) contains up to 57% of acetogenin containing isosquamocin and related compounds.

In yet another embodiment of the invention, the semisolid obtained in step (f) is dissolved in solvent selected from $CH_2Cl_2$, EtOAc and further subjecting to column chromatography using mixture of petroleum ether/ethyl acetate 9/1, 8/2 . . . 2/8, 1/9 and ethyl acetate as eluant resulting in isolation of partially purified acetogenin which are grouped into 10 sets of fractions by TLC assays.

In yet another embodiment of the invention, the ten sets of fractions obtained from column chromatography are independently subjected to semipreparative HPLC using reverse phase column RP (18 column) and methanol/water (90:10) as mobile phase using UV detection at 220 nm leading to the isolation of pure acetogenins isoquamocin, squamocin G, squamocin H, squamocin M, squamocin L, squamocin C, squamocin J, squamocin K, squamocin B, squamostatin A, squamostatin B, squamostatin C and unidentified compounds with retention times 5.88, 14.18 and 45.25 minutes.

In yet another embodiment of the invention, provides an alternative process for the preparation of an extract of seeds of *Anona squamosa* wherein in step (a), the powdered seeds are continuously percolated using a solvent at an ambient temperature through a glass column in which the powdered seeds are packed, concentrating the extract and stirring the extract so obtained with petroleum ether by 60–80° C. hexane/pentane; decanting and discarding the supernatant liquid to obtain a semisolid; and finally drying the semisolid at atmospheric pressure or reduced pressure to obtain standardized extract of the seeds of *Anona squamosa* (SESAS) having upto 57% of acetogenin comprising Isoquamocin, squamocin G, squamocin H, squamocin M, squamocin L, squamocin C, squamocin J, squamocin K, squamocin B, squamostatin A, squamostatin B, squamostatin C and the unidentified compounds with retention times 5.88, 14.18 and 45.25 minutes.

Another embodiment of the invention relates to a process, wherein the solvent used is selected from the group consisting of benzene, dichloromethane, dichloroethane, chloroform, ethyl acetate, acetone, 2-butanone, methyl tertiary butyl ether, disopropyl ether, n-butanol, acetonitrile, One more embodiment of the invention relates to a process for the preparation of stable emulsifiable concentrate, wherein said concentrate containing upto 6% isosquamocin is obtained by stirring standard extract of seeds of *Anona squamosa* (SESAS) comprising upto 57% autogenins consisting isosquamocin and related products with solvents or mixtures thereof, followed by treating with an emulsifier or emulsifier combinations to obtain a clear emulsifiable concentrate.

Another embodiment of the invention, relates to a process for the preparation of stable emulsifiable concentrate, wherein the organic solvent used is/are selected from aromax, 2-butanone, cyclohexanone, dimethyl formamide, dimethyl pthalate, dioctylpthalate, isobutanol, isobutyl methyl ketone, isopropanol, solvent C-IX and xylene individually or as suitable combination.

Still another embodiment of the invention relates to a process for the preparation of stable emulsifiable concentrate, wherein said emulsifier or emulsifier combination are selected from a commercially available ionic and non-ionic emulsifiers as Cresolox 3409, Emulsol MAL, Emellsol 172RH, Igesol, calcium alkyl benzene sulphonate (CABS), Ethylene Oxide concentrates (10 moles), Triton X100 and Tween 80.

Still another embodiment of the invention relates to a process for the preparation of stable emulsifiable concentrate, wherein the pieronyl butoxide is used as synergist.

One more embodiment of the invention provides a stable emulsifiable concentrate containing upto 30% isosquamocin of a standardized extract of seeds of *Anona squamosa* (SESAS), which is also used as insecticide or in any insecticidal formulation.

In another embodiment relates to a process of preparing fractions, said process comprising of:
1. The seeds of *Annona squamosa* are cleaned from extraneous impurities washed with water and dried at room temperature to remove the moisture.
2. The dried seeds are then ground to a coarse powder of mesh size in a suitable mill.
3. The coarse powder is packed into a column fitted with a Teflon mesh and covered with a fine cloth to prevent the escape of fine particles of the plant material into the extract
4. The plant material in the column was subjected to continuous percolation with methanol/ethanol at ambient temperature until no residue is obtained after the evaporation of a portion of the extract
5. The methanol/ethanol extract from step (4) is concentrated to a small volume at atmospheric pressure/or under vacuum
6. The concentrate from step (5) is stirred with an equal volume of petroleum ether/hexane and subjected to phase separation twice successively.
7. The dense phase from step (6) is stirred with water or solvents such as ethylacetate, 2-butanone, dichloroethane, dichloromethane, n-butanol, methylteritiarybutylether, toluene and the like and preferably ethyl acetate and subjected to phase separation.
8. The organic solvent phase was stripped of the solvent at atmospheric pressure or under vacuum and the concentrate was characterized by the analytical HPLC (FIG. 5)
9. The residue from step (8) was subjected to repetitive open column chromatography using silicagel (Acme 0.08 mm finer than 200 mesh) as a stationary phase and petroleum ether (60–80)/hexane, mixtures of hexane/petroleum ether b.p60–80° C. and ethyl acetate as mobile phase by stepwise elution (compositions 9:1, 2:8 . . . 8:2, 1:9) and ethylacetate. In another experiment, the elution was carried out with ethylacetate alone.
10. The fractions from step (9) were purified by high performance liquid chromatography using a reverse phase $C_{18}$ column as stationary phase and mixtures of methanol and water as mobile phase and pure compounds were isolated. The compounds were characterized by their retention times in HPLC, physical properties, optical rotation, CD spectra, UV spectra, IR spectra, $^1H$ NMR spectra, $^{13}C$ NMR spectra and mass spectra.
11. The concentrated extract from step 8 was stirred with organic solvents such as toluene, xylene, aromax C-IX solvent, 2-butanone, methyl isobutyl ketone, dimethylphthalate, din-octylphthalate, butanol, isobutanol and the like and emulsifiers such as Creslox for the preparation of emulsifiable concentrates. The formulations were characterized by the analytical HPLC. (FIG. 6)

12. The process of the present invention describes the preparation of an insecticidal composition devoid of undesirable constituents, which dilute the activity and interfere with the preparation of formulations under mild conditions in order to avoid the degradation of active constituents.

In the prior art, the procedure for the isolation of Annonin-I/squamocin from the seeds of *Annona squamosa* according to the U.S. Pat. No. 4,689,232, consists of (I), comminuting fresh seeds (500 g.) collected from Thailand without a solvent in a mixing unit equipped with a knife unit; (2), stirring with petroleum ether/pentane (800 ml) for 30 min each seven times; (3), filtration of seed mass; (4) stirring seed mass with ethanol/$H_2O$ (80:20) at 60° five times successively; (5), filtration of the solid components and separation of the filtrate; (6), stripping of ethanol from the filtrate resulting in an oil suspended in water; (7), extraction of the oil with diethyl ether (500 ml) 5 times each; (8), separation of diethyl ether extract; (9), removal of diethyl ether from the extract leading to a waxy mass (yield: 1.8 g. 0.36%) which is enriched in the active principle annonin-I; however, the percentage of annonin-I in this fraction and its composition was not determined; (10), 9 g of wax from step (9) was dissolved in chloroform (25 ml) and subjected to column chromatography on silicagel using mixtures of chloroform/methanol (97.5/2.5, 1–50 fractions (2.25 l) and 51–80 fractions chloroform/methanol 95/5 (1.35 lit) and fractions (37–60) gave 3.1 g (yield: 0.124%) of waxy mass enriched further in annonin i and the annonin-I content was not estimated and its composition was not determined (11), The waxy mass (200 mg.) from step (10) was subjected to preparative HPLC on a Lichroprop (RP 18 Merck R) using methanol/water/methyl tert-butyl ether/propionitrile (700: 300:150:2.5), UV detector:220 nm and the fractions of annonin-I were pooled and freed from the solvent resulting in pure annonin-I (85 mg; yield: 0.0467%). The physical properties, UV spectrum, optical rotation, IR spectrum and CD data 1H NMR data and $^1H$ noise decoupled $^{13}C$ NMR data of annonin-I are presented in comparison with squamocin reported by other workers. It should be noted that annonin-I was considered to be identical with squamocin in view of the similarities in its $^{13}C$ NMR spectra although their optical rotations annonin-I (c=0.15 in $CH_2Cl_2$) also isolated from the seeds of *Annona squamosa* $[\alpha]_D^{25}$+21.6 and squamocin (c=1.7, methanol), $[\alpha]_D^{20}$+0.15 (Y. Fujimoto, T. Eguchi, K. Kakinuma, N. kakawa, M. Sahai and Y. K. Guptha, Chem. Pharm. Bull., 36, 4802, 1988) differed. Similar discrepancies in optical rotation have also been encountered with a compound considered to be identical with squamocin (c=0.94, MeOH, $[\alpha]_D$+14.9 (K. Kawazu, J. P. Alcantara and A. Kobayashi, Agric. Biol. Chem., 53, 2719, 1989). Subsequently the $^{13}C$-NMR spectrum of squamocin was reported along with the closely related compounds squamocin-B, squamocin-C, squamocin-D, squamocin-E, squamocin-F, squamocin-G, squamocin-H, squamocin-I, squamocin-J, squamocin-K, squamocin-L, squamocin-M, squamocin-N. In this paper, the optical rotation $[\alpha]_D$ of squamocin was not reported and the absolute configuration of the methyl group at C-36 was shown to be 'S' by chemical degradation and its CD spectrum showed peak at $\lambda_{236}$ ($\Delta\epsilon$–0.45 in MeOH). However the $^{13}C$ NMR spectrum of squamocin showed signals for 2 carbons at δ 28.9 and δ 25.7. (M. Sahai, S. Singh, M. Singh, Y. K. Guptha, S. Akashi, R. Yuji, K. Harayama, H. Asaki, H. Araya, N. Hara, T. Eguchi, K. Kakinuma, N. Ikekawa and Y. Fujimoto, Chem. Pharm. Bull. 42, 1163, 1994) were split into signals at δ 28.99 and δ 28.96 and δ 25.69 and δ 25.65 respectively in the earlier reports of 13 $_C$ NMR spectra of squamocin (Y. Fujimoto, T. Eguchi, K. Kakinuma, K. Ikekawa, M. Sahai and Y. K. Guptha, Chem. Pharm. Bull, 36, 4802, 1988 and Y. Fujimoto, C. Murasaki, K. Kakinuma, T. Eguchi, N. Ikekawa, M. Furuya, K. Hirayama, T. Ikekawa, M. Sahai, Y. K. Guptha, A. B. Ray, Tetrahedron Letters, 31, 535, 1990). Thus, the samples of squamocin of Sahai et al and Fujimoto et al are different since their $^{13}C$ NMR spectra are not identical. Duret et al have also noticed the discrepancies in the optical rotations of squamocin $[\alpha]_D$+16.3 (P. Duret. These de Doctoratde l'Universite Paris-Sud, Chatenay-Malabry, 1997) and $[\alpha]_D$+24 (P. Duret, B. Figadere, R. Hocquemiller and A. Cave, Tetrahedron Letters, 38, 8849, 1997). When the sample of squamocin having optical rotation $[\alpha]_D$+24 was heated for 16 hours in methanol the optical rotation was not changed; however, it was changed to +9 after treatment with diethylamine due to epimerisation of methyl group at C-36 position. They concluded that $[\alpha]_D$ is dependent at the first level on the absolute configuration of methyl at C-36 position and single epimerisation of THF core leads only to a slight change in value. They have observed that the two epimers are inseparable by HPLC and they have identical UV, IR, $^1H$ and C NMR spectra and mass spectra and differ in their optical rotation. Thus, it appears that the squamocin reported by Fujimoto et.al which has two carbon signals each at δ 28.99 and δ 28.96 and two carbon signals at δ 25.69 and 25.65 $[\alpha]_D$+0.15 (c, 1.5 MeOH) has a 'R' configuration for the methyl group at C-36 position; whereas the squamocin whose optical rotation was not reported and which has only one signal at δ 28.9 and δ 25.7 for two carbons each has a 'S' configuration. Annonin-1 was also shown to have 36 S configuration but it has two carbon signals each at δ 28.91 and δ 28.891 and δ 25.597 and 25.573. The optical rotation of Annonin-I in $CH_2Cl_2$ was reported $[\alpha]_D^{25}$+21.5 (c=0.15 in $CH_2Cl_2$, CD spectrum showed $\lambda$=239 nm, $\Delta\epsilon$=–0.55, 210 nm, $\Delta\epsilon$=+5.70). Furthermore, the absolute stereochemistry of Annonin-I was determined as 36 S in comparison with model compounds, (A. Gypser, C. Bulow, H. Scharf, Tetrahedron, 51, 1921, 1995). Thus Annonin-I and squamocin of Sahai et al which differ in their $^{13}C$ NMR spectra differ in the stereochemistry of the hydroxyl at C=28 position having the absolute configuration 'R'. Since the carbon connectivity of squamocin of Sahai et al and Annonin-1 are same, they have to differ in their stereochemistry in the core and it requires some more investigation. In prior art, a compound described as light yellow oil $[\alpha]_D^{23}$=+21.25 (c=0.004 g/ml, $CHCl_3$, $MH^+$ 623.4838, $C_{37}H_{67,8}$) from the bark of *Annona bullata* (Y.-H. Hui, J. K. Rupprecht, J. E. Anderson, K. V. Wood and J. L. Mc Laughlin, Phytotherapy Research, 5, 124, 1991) was considered to be squamocin reported by Fujimoto et al $[\alpha]_D$+0.15 (c=1.5, MeOH) cited earlier by comparing the $^1H$ NMR and $^{13}C$ NMR data and TLC behavior in two solvent systems and their optical rotations were not considered. Thus, squamocin of Hui et al $[\alpha]_D^{23}$+21.25 (c=0.04 g/ml. $CHCl_3$) differs from that of Fujimoto et al $[\alpha]_D$+0.15 (c=1.5, MeOH and these two compounds are likely to be epimers at C-36 position, A compound considered to be identical with squamocin ($[\alpha]_D$ not reported) having a $^{13}C$ NMR spectrum (δ 25.6 and 25.5). Similar to squamocin reported by Hui et al with two signals at (δ 25.577 and 25.544) was assigned one of the alternate structures. (A. Hisham, L. A. C. Pieters M. Clayes, E. Esmans, R., Bommisse and A. Vlitink, Phytochemistry, 39, 545, (1991).

In the prior art, Sahai et al (Chem. Pharm. Bull. 42, 1163, 1994) isolated squamocin and related compounds, squamocin-B, squamocin-C, squamocin-D, squamocin-E, squamocin-F, squamocin-G, squamocin-H, squamocin-I, squamocin-J, squamocin-K, squamocin-L, squamocin-M and squamocin-N, squamostatin-A, squamostatin-B, squamostatin-C, squamostatin-D and squamostatin-E from the seeds of Annona squamosa involving the following steps, (1), ground seeds of Annona squamosa (1 kg.) were subjected to extraction with petroleum ether (b.p. 60–80° C.) in a soxhelet and the petroleum ether extract was allowed to stand at room temperature for 24 hrs; (2), the supernatant was decanted and the oily residue was washed with petroleum ether; (3), petroleum ether washings were combined with the supernatant and partioned with MeOH-$H_2O$ (10:1); (4), the lower o phase from step 3 was concentrated; (5), the residue from step 4 was digested with ethylacetate; (6) the ethyl acetate soluble portion was separated and concentrated to give a residue as an oil (8.1 g) (0.81%); using $CHCl_3$-EtOAc gradient system and EtOAc-MeOH gradient system; (7) the oil was chromatgraphed on a silica gel column into a least polar fraction, moderately polar fraction and polar fraction; (8), least polar fraction was rechromatographed on silica gel (benzene-ethyl acetate mixtures) resulting in a nonpolar fraction; (9) the non polar fraction from step 8 was subjected to reverse phase preparative HPLC on a ODS column using MeOH/$H_2O$(1:1); (10), when mixtures were obtained in step 9 preparative HPLC was carried out with acetonitrile/$H_2O$ (10:1) or by preparative TLC resulting in the isolation of squamocin-B, squamocin-C, squamocin-D, squamocin-E, squamocin-F, squamocin-G, squamocin-H, squamocin-I, squamocin-J, squamocin-K, squamocin-L, squamocin-M and squamocin-N. The yields of the above compounds ranged from 10 mg (squamocin-J) to 70 mg (squamocin-K); (11), the polar fraction on preparative HPLC gave squamostatin-A, squamostatin-B, squamostatin-C, squamostatin-D and squamostatin-E.

In the prior art, Fujimoto et al described the isolation of squamocin from the powdered seeds of Annona squamosa collected from Varanasi, India in the following steps; (1), extraction of pulverized seeds with petroleum ether (b.p. 60–80° C.); (2), concentration of the petroleum ether extract; (3), separation of waxy semisolid and the supernatant; (4), washing the waxy semi solid of step 3 with petroleum ether; (5), subjecting the resulting waxysolid from step 4 to Sigel column chromatography (eluent: 97/3, $CHCl_3$/MeOH, v/v) to a nearly homogeneous oil which was subjected again to Sigel column chromatography leading to pure squamocin (2.2 g) having an optical rotation $[\alpha]_D^{2o}$+0.15 (c=1.7, MeOH), continued elution of the column, yielded squamostatin-A (15 mg, Fujimoto et al, Tetrahedron Letters, 31, 535, 1990), squamostatin-B, squamostatin-C, squamostastin-D and squamostatin-E (M. Sahai et al, Chem. Pharm. Bull. 42, 1175, 1994). In this paper, the quantity of seeds of Annona squamosa was not described and as such the yield of squamocin cannot be ascertained. The waxy semisolid after concentration of the petroleum ether (b.p. 60–80° C.) extraction of the pulverized seeds followed by washing with petroleum ether is a candidate for commercial exploitation if squamocin has insecticidal activity and its insecticidal activity was not determined, although squamocin was shown to possess cytotoxic activity against Le Hela cells. Further more, the chemical composition of product from 4 was not established and it contained compounds such as squamostatin-A, squamostatin-B, squamostatin-C, squamostatin-D and squamostatin-E and squamostene.

In summary, annonin-I described in the U.S. Pat. No. 4,689,232 and squamocin reported by Fujimoto et al differ in their optical rotation. Squamocin reported by Fujimoto et al and Kawazu et al also differ in their optical rotation. Squamocin reported by Fujimoto et al also differs in optical rotation from squamocin reported by Hui et al. Squamocin reported by Fujimoto et al also differs from that of squamocin reported by Sahai et al in its $^{13}C$ NMR spectrum while the $[\alpha]_D$ of this sample was not determined. Thus, squamocin (Fujimoto), squamocin (Kawazu). Squamocin (Hui), squamocin (Sahai) and annonin-I are not the same. We also consider annonin-I $[\alpha]_D^{25}$+21.50 (c=0.15 in $CH_2Cl_2$) and squamocin (Hui) $[\alpha]_D^{23}$+21.25 (c=0.04 g/mg in $CHCl_3$) as it. We designate squamocin reported by Sahai et al as isosquamocin in view of its differences in $^{13}C$ NMR spectrum with squamocin (Fujimoto)

In the prior art the U.S. Pat. No. 4,689,232 also described a process for the isolation of annonin-I possessing insecticidal properties. The process consists of (1) comminuting the seeds of Annona squamosa (500 g); (2), stirring with petroleum ether (800 ml; 30 min), 7 times successively; (3), stirring the filtered seed mass with EtOH-$H_2O$ (8.2 at 65° C.) five times successively; (4), stripping of ethanol from filtered combined ethanol-$H_2O$ extra ts; (5), treatment of the oily residue with ether (500 ml, 5 times); (6), concentration of ether extract giving rise a waxy mass (1.8 g, 0.36%); (7), column chromatography of the product from step 6 (silica gel) using $CHCl_3$-MeOH (97.5/2.5) and $CHCl_3$-MeOH (95/5); (8), pooling of fractions containing annonin-1 leading to a waxy mass (yield 0.062%); (9) preparative HPLC of waxy mass from step 8 using a Lichroprep $RP_{18}$ Merck R using MeOH/$H_2O$-methyl tertiary butyl ether-propionitrile (7:3:1.5:0.025); (10), pooling of fractions containing annonin-1 and stripping of the solvent leading to annonin-1 in an yield of 0.026%. Furthermore, it is stated that crude annonin obtained from the comminuted seeds of Annona squamosa involving (1), extraction with petroleum ether for the removal of petroleum ether constituents; (2), extraction of the residual seed mass with water miscible alcohols and if appropriate in presence of water; (3), concentration of the alcohol extract; (4) extraction of concentrate form step 3 with aliphatic halogenohydrocarbon/or an ester and (5), evaporation of the extract from step 4 resulting in crude annonin-1.

The process of the U.S. Pat. No. 4,689,232, also claims a process wherein (1), comminuted seeds are first extracted with petroleum ether followed by (2), extraction of residual seed mass with $CH_2Cl_2$ or $CHCl_3$ or diethyl ether or ethylacetate or mixtures thereof, and (3), evaporation of the solvent from the extract from step 2 resulting crude annonin-1 and crude annonin-I is suitable for combating pests. It is also claimed that formulations contain annonin-1 between 0.1 and 95% and the active compound concentration of the use forms can be from 0.0000001 to 95% by weight of annonin-I.

It is therefore necessary to determine the annonin-1 content of crude annonin and its formulations and to characterize the other constituents accompanying crude annonin-I, It is also desirable to simplify the process of extraction of crude annonin-I from the seeds of Annona squamosa by direct extraction with polar solvents such as ethanol, ethanol-water, ethylacetate, chloroform etc. eliminating the initial extraction with petroleum ether. In the present invention, the extraction from the seeds of Annona squamosa with petroleum ether is eliminated and direct extraction of ground seeds is carried out with solvents such as methanol or ethanol or with compositions having water at ambient temperature. Under these conditions, the petroleum ether soluble inactive compounds are retained with the plant material and the polar active compounds are extracted into polar solvents such as methanol. In the present invention the major active principle was characterized as a new compound designated as Isosquamocin (28 epiannonin-I) and it was different from annonin-I in its $^{13}$C NMR spectrum in CDCl$_3$ and it possessed remarkable insecticidal activity reminiscent of annonin-I. In the present invention, Isosquamocin (28-epi annonin-I) content was found to be in the range of 25–55%. The present invention also describes a simple process for the preparation of a standardized extract of the seeds of *Annona squamosa* enriched in isosquamocin.

In the present invention the compounds accompanying isosquamocin (28-epi annonin-I) in the standardized extract of the seeds of *Annona squamosa* were prepared by repetitive column chromatography (sigel) and HPLC C-18 column and characterized by their mass spectra, H and C NMR spectra as squamocin-B, squamocin-C, squamocin-G, squamocin-H, neoannonin, squamocin-K, squamocin-M, squamocin-N, squamostatin-A, bullatalicin, bullatanocin and three other related compounds with retention times, 5.88 min 14.18 min and 45.28 min in HPLC.

In the present invention, the standardized extract of seeds of *Annona squamosa* is formulated as an emulsifiable concentrate and standardized with respect to isosquamocin (28-epiannonin-I. FIG. 6)

Thus, the present invention discloses a new organic compound isomeric with annonin-I which is now designated as isosquamocin (28-epiannonin-I) and which possesses insecticidal properties reminiscent of annonin-I from the seeds of *Annona squamnosa*. The present invention also describes a simple process for the preparation of a standardized extract of seeds of *Annona squamosa* enriched in isosquamocin (28-epiannonin-I). In the present invention, many of the active constituents present in the standardized extract of the seeds of *Annona squamosa* were characterized as squamocin-B, squamocin-C, squamocin-G, squamocin-H, squarnocin-J (neoannonin), squamocin-K, squamocin-L, squamocin-M, squamocin-N, squamostatin-A, bullatalicin, bullatanocin and three related unidentified compounds with retention times 5.88 min, 14.18 min and 45.28 min in HPLC which were characterized by H NMR and $^{13}$C NMR spectra and mass spectra. In the present invention, isolation of pure isosquamocin (28-epiannonin-I), squamocin-B, squamocin-C, squamocin-G, squamocin-H, (neoannonin), squamocin-K, squamocin-L, squamocin-M and squamocin-N, squamostatin-bullatalicin and bullatanocin and three related compounds with retention times 5.88 min, 14.18 min and 45.18 min by silica gel column chromatography and reverse phase HPLC (C-18 column) from the standardized extract of the seeds of *Annona squamosa* is also described.

In the present invention, standardized emulsifiable concentrate formulation of isosquamocin (28-epiannonin-1) and accompanying constituents is also described.

In the prior art, Born et al (L. Born, F. Lieb, J. P. Lorentzen, H. Moeschler, M. Nonfon, R. Solner and D. Wendisch, *Planta Medica*, 56, 312, 1990) reported the isolation of annonin-I (yield: 0.01%) asimicin (yield: 0.001%) and annonin-VI (0.0005%) from the seeds of *Annona squamosa*. The process consists of the following steps: (1), pulverized seeds of *Annona squamosa* (120 kg) were extracted with ligroin; (2), the ligroin extract was concentrated and the concentrate was partitioned with MeOH/H$_2$O (95/5) and phases were separated; (3), the concentrate of the MeOH/H$_2$O phase from step 2 was treated with petroleum ether and the petroleum ether extract was separated; (4), the petroleum ether extract from step 4 was subjected to adsorption column chromatography successively using XAD®-Harz (Rohm & Haas) resin leading to fractions containing annonin-I asimicin and annonin-VI *Annonacin, annoacin*-A and *Annonastatin*. Pure annonin-I, colorless amorphous solid (12 g) annonin-VI, colorless annonin VI, colorless waxy solid (600 mg) asimicin, waxy solid (1.3 g) annonacin (220 mg), annonsastatin (120 mg) as colorless amorphous solids isolated from these fractions using column chromatography (silicagel, eluent: CHCl$_3$→CHCl$_3$/MeOH, v/v, MeOH; and HPLC using a reverse phase Lichrrosorb RP 18 column, eluent: MeOH/H$_2$O/n-propanol, 85/15/5 for annonin-I, asimicin and annonin VI; acetonitrile/H$_2$O/n-propanol, 80/20/5 for annonastatin, acetonitrile/H$_2$O/dioxan, 70/30/2 for annonacin and methanol/H$_2$O/dioxan, 60/40/8 for annonacin A. Of these, annonacin, annonacin A and annonasatin contain only one tetrahydrofuran ring and annonin-I, annonin-VI and asimicin contain adjacent bis tetrahydrofuran skeleton. Annonacin, annonacin A and annonastatin showed good anthelmintic activity against the nematode Caenorhabditis elegans and the insect phaedon cocholeriac (F. Lieb, M. Nonfon, U. N. Neuman and D. Wendisch, *Planta Medica*, 56, 317 (1990).

In the prior art ground seeds of (Lobo, Batangas, Luro island) *Annona squamosa*, yielded four compounds designated as annonin-IV, annonin-VII, annonin-XIV and annonin-XVII in addition to annonin-I, annonin-VI, asimicin, annonacin, annonacian-A and annonastatin in the following steps (1), ground seeds were extracted with methanol; (2), the methanol extract was concentrated by evaporation of the solvent; (3), the residue was partitioned between petrol and water to remove the polar constituents; (4), the petrol extract was chromatographed on XAD® resin (Rhiom and Haas); (5), fractions containing annonin-IV, annonin-VIII, annonin-1, annonin-VI, annonin 14, annonin 16, annonin-1 annoni-6 asimicin, annonacin, annonacin-A and annonastatin from step 3 purified successively by column chromatography (si gel) and HPLC RP-18 column giving rise to Annonin-IV (1.5 g.), amorphous wax m.p. 107–8° C. M$^+$+H.639 $[\alpha]_D^{25}$+13.6 (CH$_2$Cl$_2$; c 0.28); annonin-VIII, amorphous wax (2.5 g) m.p. 113.6° M$^+$+H, 639 waxy $[\alpha]_D^{25}$+9.8 (CH$_2$Cl$_2$, c=0.29; Annonin XIV, amorphous waxy (44 mg) $[\alpha]_D^{25}$+15.7(CH$_2$Cl$_2$, c=0.30), Annonin XVI, amorphous wax (1 g) m.p. 121–3°, M$^+$+H. 639 $[\alpha]_D^{25}$+15.9°(c=0.21) (M. Nonfon, F. Live, H. Moeschler sand D. Wendisch, *Phytochemistry*, 29, 1951, 1990) and their structures were revised as bullatanocin, bullatalicin and squamostatin-A respectively, (X,-P. Fang, Z.-M. Gu, M. J. Reiser, Y.-H. Hui and J. L. Mc Laughlin, *Journal of Natural Products*, 56, 1095, 1994) and they belong to the category of non adjacent bis tetrahydrofuran derivatives. Of these, bullatalicin was found to possess insecticidal properties (F. Q. Alali, W. Kaakesh, G. W. Bennett and J. L. McLaughlin, *J. Econ. Entomol.* 91, 642, 1998 and K. He. L. Zeng, Q. Ye, G. Shi, N. H. Oberlies, G.-X. Zhao, C. J. Njoku and J., L. Mc Laughlin, *Pesticide Science*, 49, 372, 1997). Bullatalicin also showed selective cytotoxic activities for certain human tumor cell lines with ED$_{50}$ values as low as 10$^{-7}$ ug/ml (Y. H. Hui, J. K. Rupprecht, J. E. Anderson, Y. M-Lu, D. L. Smith, C.-J. Chang and J. L. Mc Laughlin, *Tetrahedron*, 45, 6941, 1989) and it has shown very good efficacy comparable with that of cisplatin (K. I. Ahmedasahib, R. M. Hollingworth, J. P. Mc Govern, Y. H. Hui and J. L. Mc Laughlin, *Life Sciences*, 53, 1113, 1993). It was also found to be cytotoxic to multidrug resistant human mammary carcinoma MCF-7/Adr cells (W. H. Oberlies, C.-J. Chang and J. L. Mc Laughlin, *J. Nat. Prod.* 59, 994, 1996) Bullatalicin and bullatanocin have been shown to be about 10,000 times more as toxic as adriamycin for the colon cell line (H-29) and lung cell line (A-549) and they are powerful inhibitors of complex$^{-1}$ of mitochondrial transport systems (Z. M. Gu, X.-P. Fang, M. J. Reiser, Y. H. Hui, L. R. Meishbauer, D. L. Smith, K. V. Wood and J. L. Mc Laughlin, *Tetrahedron,* 49, 747, 1993). Some of these results are subjects of Patent applications WO95,34,544 and U.S. Appl. 259,383 (*C A,* 124, 256011 n,) squamostalin-A also showed in vitro cytotoxic activity against L-5178 Y (IC$_{50}$, 0.5 ug/ml (Y. Fujimoto, C. Murasaki, K. Kakinuma, T. Eguchi, N. Ikekawa, M. Furuya, K. Hirayama, T. Ikekawa, M. Sahai, Y. K. Guptha and A. B. Ray, *Tetrahedron Letters,* 31, 535, 1990). Japanese Patent JP 0,341,076 claimed squamostatin-A and its analogues as anticancer agents.

A comparison of the results of the present invention and those of Lieb et al show the following differences; (1), the source of the seeds of *Annona squamosa* is different; (2), the solvents used for the extraction of the ground seeds are different (MeOH, present invention; aq.methanol, Lieb et al; (3), the purified crude petroleum ether extracts obtained from the concentrate of aq.methanol extract by partition with petroleum ether and water contained the desired constituents in the procedure of Lieb et al. In the present invention, the methanol concentrate is first partitioned with petroleum ether and then with a composition of water and ethyl acetate. Petroleum ether partially extracted desired compounds, while ethyl acetate extracted the desired compounds exhaustively. The concentrate of the ethyl acetate extract constituted the insecticidal composition.

In the prior art, Kawazu et al (K. Kawazu, J. P. Alcantra and A. Kobayashi, *Agric. Bioll. Chem.* 53, 2719 1989), isolated two compounds designated as squamocin and neoannonin possessing insecticidal activity from the seeds of *Annona squamosa* in the following steps; (1), air dried ground seeds of *Annona squamosa* (2.1 kg) was subjected to extractions with (a), hexane and (b) ethyl acetate successively. The concentrate of the active ethyl acetate extract (366 g) was partitioned with 10% aq.methanol and n-hexane. The active aq.methanol layer was concentrated and the concentrate was subjected to chromatography leading to the isolation of squamocin [α]$_D^{22}$+14.9 (c=0.94, MeOH) and neoannonin. It has to be remembered that the optical rotation of squamocin originally reported was [α]+0.15 (MeOH, c=1.5). We believe that they are different compounds.

The main active compound isosquamocin of the present invention has been characterized on the basis of its physical and spectral properties.

1. Physical appearance: Colorless amorphous waxy solid, m.p. 45° C.
2. Solubility: The waxy substance is insoluble or very sparingly soluble in petroleum ether/hexane and water and readily soluble in ether, chloroform, dichloromethane, acetone, methanol and ethyl acetate.
3. Molecular weight: 622, the molecular weight was determined by FAB mass spectrum, M$^+$+H, 623.489 and elemental composition was determined as $C_{37}H_{67}O_7$.
4. UV Spectrum: Acetonitrile $\lambda_{max}$207 nm ($\epsilon_{max}$, 9,000)
5. I.R. Spectrum: $V^{KBr}_{max}$ "3414, 2829, 2853, 1747, 1647, 1485, 1389, 1373, 1319, 1289, 1275, 1248, 1201, 1172, 1145, 1120, 1079, 1027, 1000, 980, 960, 929 Cm$^{-1}$.
6. EI mass spectrum: m/e (intensity) 604.4 (0.6, M$^+$-H$_2$O),. 586.3 (0.6, M$^+$-2 H$_2$O), 568.3 (0.7, M$^=$-3H$_2$O), 519.3 (2.6), $C_{31}H_{51}O_6$; 501.3 (2.4), $C_{31}H_{49}+0_{0.5}$; 436.2 (2.7), 435.2 (3.2), $C_{26}H_{43}O_5$; 418.2 (4.0),. 417.2 (6.4),. $C_{26}H_{41}O_4$. 400.2 (2.9), 399.2 (9), $C_{26}H_{39}O_3$; 365.2 (7.8); $C_{22}H_{37}O_4$; 349.2 (6.4), 348.2 (14.2); 347.2(57.6), $C_{22}H_{35}O_3$; 330.2 (2.7), 329.2 (10.4), $C_{22}H O_2$; 321.1 (5.3), 3.19,.2 (2.2), 310.2 (5.3), 309.1 (4.8), 307.1 (2.0), 297.1 (5.3), 295.1 (100), $C_{18}H_{31}O_3$, 293.1 (3.2), 291.1 (3.8), 267.1 (1.9), 266.1 (2.4), 265.1 (2.4), 257.1 (1.2), 239.1. (15.7), $C_{15}H_{27}O_2$ 211.7(0.6), $C_{14}H_{27}0$; 208.1 (3.8), 203.1 (3.1), 195.1 (6.8), 169.1 (10), 168.1 (8.4), 167.0 (2.8), 153.0 (3.1), 151.1 (5.9), 149.1 (3.7), 147 (2.3), 143.1 (4.4), 142 (2.4), 141.0 (8.2), 140(2.8), 139 (4.3), 137.1 (4.5), 135.1 (6.3), 133.0 (3.2), 127 (2.1), 125.0(9.2), 124.0 (2.8), 123.0 (8.1), 122.0 (2.6), 121.0 (9.1), 119.0 (3.0), 113.0 (8.3), 112.0 (7.8), 111.0 (9.1), 110.0 (9.4), 109.0 (19.,1), 108.0 (2.5), 107.0 (8.5), 105.0 (2.8), 101.0(2.0), 100.0 (2.3), 99.0 (1.1), 98.0(4.1), 97.0(21.6), 96.0(26.4), 95.0(26.7), 94.0(5.1), 93.0 (9.8), 91.0 (3.4), 85.0 (6.4), 84 (5.9), 83.0 (21.5), 821.0 (6.4), 81.0 (27.2), 80.0 (3.9), 79.0 (9.0), 71.0 (22.1), 70.0 (7.1), 69.0 (20.5), 68.0 (6.8), 67.0 (23), 58.0 (3.7), 57.0 (14.1), 56.0 (3.4), 55.0 (30.5), 54 (3.7), 53 (2.7), 45 (2.0), 44 (3.2), 43.0 (16.7), 41.0 (18.2). $^{13}$C NMR spectrum (CDCl$_3$) $\delta_{ppm}$: 173.862 (>C=0) 148.838 (CH), 134.247(quat C), 83.338 (CH), 82.781 (CH), 82.492 (CH), 82.172 (CH), 77.638 (CH), 74.129 (CH), 71.683 (CH), 71.288(CH), 37.415 (CH$_2$), 37.212 (CH$_2$), 33.108 (CH$_2$), 32.392 (CH$_2$), 31.888 (CH$_2$), 29.712 (CH$_2$), 29.561 (3×CH$_2$), 29.546 (CH$_2$), 29.454 (CH$_2$), 29.338(CH), 29.251(CH), 29.124(CH), 28.935 (2×CH+2), 27.335 (CH$_2$), 25.608 (2×CH$_2$),. 25.116 (CH$_2$), 24.707 (CH$_2$), 22.578 (CH$_2$), 21.985 (CH$_2$), 19.164 (CH$_3$), 14.042 (CH$_3$). $^1$H NMR spectrum (CDCl$_3$) δ(ppm): 6.9, dd, J=1.75 Hz(1H), 4.99,q,q, J=7 Hz and 1.75 Hz (1H); 3.79–3.97, m (5H); 3.60, s,b.r (1H), 3.398, m (1H). 2.64, s (1H, O H exchangeable with D$_2$0); 2.28 signal overlapped with other signals (1H, exchangeable with D O), 2.264, t,t, J=7.66 and 1.75 Hz (2H); 1.93–2.05, m (3H); 1.78–1.93, m(2H), 1.58–1.72, m, 4H; 1.407, d, J=6.56 H$_z$ (3H); 1.36–1.48, m, 1.18–1 (25H), 0.882, t, J=6.78 (3H).

Optical rotation: c=0.01003 g/m in CH$_2$Cl$_2$ λ 589, 578, 546, 436, 365 and 302:

[α]=+18.25, +20.87, +23.79, +44.37, +80.68, and +164.08 respectively

[α]$_D^{25}$ c=0.00655 g/ml, CHCl$_3$, +20.61

[α]$_D^{25}$ c=0.01326 g/ml; MeOH, +15.98

Circular Dichroism: Methanol

λ=239 (Δε=−0.55); λ=210 nm (Δε=5.7), λ=240.5, (Δε=−0.68)

Acetonitrile

λ=240 (Δε=−0.44); λ=201 nm (Δε+8), λ=199, (Δε+8)

Isosquamocin [α]$_D^{2o}$ c=0.01326 g/ml MeOH 15.98 differs from squamocin in its optical rotation [α]$_D^{2o}$+0.15 (c=1.7, MeOH) Isoquamocin also differs from squamocin in its $^{13}$C NMR spectrum. The signals at δ 28.99 and 28.96 and at δ 25.69 and 25.65 in the case of squamocin coalesced and they were observed at 28.935 and 25.608 respectively for isosquamocin (T. Eguchi, K. Kakinuma, M. Ikekawa, Sahai and Y. K. Guptha *Chem. Pharm. Bull.* 48, 4802, 1988). These differences $^{13}$C NMR spectra of isosquamocin and squamocin persist with isosquamocin and annonin-I described in the U.S. Pat. No. 4,689,232. Thus, isosquamocin is isomeric with both squamocin and annonin-I in view of the close resemblance's in their molecular formula, mass spectra UV, spectra, IR spectra, $^1$H NMR spectra, optical rotation and circular dichroism data and subtle differences in their $^{13}$C NMR spectra. These results suggest that isosquamocin has the same molecular skeleton as annonin-I and it differs from annonin-I in the stereochemistry of the hydroxyl at the C-28 position due to epimerisation suggesting the absolute stereochemistry 15R, 16R, 19R, 20R, 23R, 24S, 28S, 36S at the chiral centres.

The new compound isosquamocin, the standardized extract of the seeds of *Annona squamosa* (SESAS) containing isosquamocin (1) and related compounds squamocin-G (2), asimicin/squamocin-H, (3), 4-deoxyasimicin/squamocin-M (4), desacetyluvarian/squamocin-L (5), motrilin/annonin-III/squamocin-C (6), neoannonin/squamocin-J (7), squamocin-K (8), squamocin-B (9), squamostatin-A (10), bullatalicin/squamostatin-B (11), bullatanocin/squamostatin-C/annonin-IV/cherimolin-II (12) and unidentified compounds with retention times 5.88 min, 14.18 min, and 45.25 min. in HPLC and the formulations of the standardized extract of the seeds of *Annona squamosa* have been found to possess biological properties which enable them to be used for the control of insect pests and for the treatment of cancer.

Furthermore, it has been found that isosquamocin and the related compounds (2) to (12) and three unidentified compounds and the standardized extract of the seeds of *Annona squamosa* (SESAS) consisting of isosquamocin (1) and related compounds (2) to (12) and three unidentified compounds is prepared by a process in which the seeds of *Annona squamosa* are used in the following steps.

1. Dry seeds are disintegrated into a coarse powder in a multimill (Gannon private Ltd, Bombay, India);
2. The seed powder from step 1 is packed into a column and percolated continuously with water miscible aliphatic alcohols such as methanol, ethanol, n-propanol and suitable compositions of these solvents with water and the extract is concentrated;
3. The extract obtained in this manner is stirred twice successively with petroleum d-ether b.p. 60–80° C./hexane and the petroleum ether phases, were combined and concentrated resulting in a semisolid and its HPLC is shown in FIG. 5.
4. The heavier phase from step 3 is stirred with suitable quantities of water and water immiscible solvents such as ethylacetate, 2-butanone, methyl tertiary butylether, dihloromethane, chloroform, dichloroethane, benzene and toluene twice successively and the phases were separated;
5. The organic solvent phases are combined and concentrated resulting in oily residue which is designated as standardized extract of the seeds of *Annona squamosa* (SESAS) and its HPLC is shown in FIG. 5. SESAS has been found to contain isosquamocin upto 48% and the related compounds (2) to (12) and three unidentified compounds mentioned earlier.
6. Alternatively the seed powder from step 1 is packed into a column and continuously percolated at ambient temperature with solvents such as benzene, dichloromethane, chloroform dichloroethane, ethylacetate, acetone, 2-butanone, methyl tertiary butyl ether, disopropyl ether, ethylacetate, n-butanol and acetonitrile (2) the extract is concentrated and the concentrate diluted with petroleum ether b.p.60–80° C./hexane/pentane and the supernatant liquid is decanted and discarded. The resulting semisolid is free of solvents by drying at atmospheric pressure or reduced pressure, and it is the standardized extract of the seeds of *Annona squamosa* (SESAS) containing upto 57% of isosquamocin and compounds (2) to (15) and its HPLC is shown in FIG. 5.
7. The standardized extract of seeds of *Annona squamosa* from step (5) or (6) is subjected to column chromatography (Sigel) using petroleumether, b.p. 60–80° C., petroleumether/ethyl acetate, 9/1 8/2 . . . 2/8, 1/9 as eluents by stepwise elution resulting in fractions which were pooled by thin layer chromatography (Sigel).(TLC)
8. Fractions from step (7) are individually subject to semipreparative HPLC using reverse phase C18 column and methanol/water as the mobile phase using UV detection at 220 nm leading to the isolation of isosquamocin and compounds (2) to (12) and three unidentified compounds.
9. The standardized extract of the seeds of *Annona squamosa* prepared by steps (5) or (6) is stirred with solvents (such as toluene xylene C-IX, aromax, ethanol, n-propanol, isopropanol, n-butanol, isobutanol, 2-butanone methylisobutylketone, cyclohexanone, ethylacetate, dimethyl phthalate, di n-octyphthalate, acetonitriledimethyl sulfoxide, dioxan, dimethyl formamide, water or suitable mixtures emulsifiers such as polyoxyethylene sorbitan oleate, tween-80, polyethylene glycol-tert-octyl phenylether, Tritonx 100; Calcium alkyl benzene sulfonate (CABS or Igesol, blend of aninoic and nonionic surfactants such as creslox 3409, emulsol MAL; blend of nonionic surfactants such as emulsol 172 RH; and ethylene oxide condensates and the syngerists such as piperonyl butoxide optionally.

The formulations contain 1 to 30% of isosquamocin. In actual use forms, the formulations are active at 1 ppm to 10,000 ppm depending upon the nature of the pests species and intensity of the infestation of insect pest population. The active principles and their formulations according to the invention can be present as a mixture with other active compounds, such as insecticides, acarcides, nematicides, fungicides growth promoters and herbicides. These insecticides include for examples azadirachtin, azadirachtin containing neem seed extract and other pesticidel plant extracts. *Bacillus thuringiensis*, other synthetic pesticides like organic carbamates, organophsphates, phenyl ureas, pyrethroids and substances produced by microorganisms.

The formulations contained 0.1 to 30% isosquamocin. In actual use forms the formulations are active at 1 ppm to 10,000 ppm depending on the nature of insect pest species and intensity of infestation of the insect pest population. The insect pests belonging to a broad spectrum of insect orders and phyto parasitic nematodes are controlled by these formulations. Some of the insect pests of the crops such as cotton, groundnut sorghum, sugarcane, tomato, brinjal, chillies cabbage, pigeonpea, chickpea, are controlled by these formulations. They are also found to control the larvae of mosquitoes and houseflies and cockroaches.

The preparation of standardized extract of the seeds of *Annona squamosa* (SESAS), its active principles and their formulations are illustrated with the aid of the following examples and they do not limit the scope of the invention.

EXAMPLE 1

The seeds of *Annona squamosa* (10 kg) were disintegrated in a multimill (Gannon Private Ltd., Bombay, India) to a coarse powder having particle size ranging from BSS-7 (0.12 mm) to BSS-72 (2.4 mm) and the powder was packed into a glass column. The column containing the powder of seeds of *Annona squamosa* was then continuously extracted by percolation with methanol (40 l) at ambient temperature. The resulting extract (36 l) was concentrated at atmospheric pressure or under reduced pressure and the concentrated (1.761.) was stirred twice, successively with an equal volume of petroleum ether b.p. 60–80° C./hexane in a stirred vessel and petroleum ether/hexane phases were separated in a phase separator and concentrated resulting a semisolid (13.5 g). The heavier phase was stirred with ethyl acetate (1.6 l) for 15 minutes and water (0.8 l) in a stirred vessel. The lighter ethyl acetate and heavier aqueous phases were separated in phase separator. The heavier phase was stirred again with ethyl acetate (2.4 l) and both the ethyl acetate phases were combined and the solvent was removed at atmospheric pressure or under reduced pressure resulting in a brown semisolid which was designed as standardized extract of seeds of Annona squamosa (SESAS) (200 g) and it was found contain 38.89% of isosquamocin by analytical HPLC using a reverse phase $C_{18}$ column (U bond pack LC 18 3.0×150 mm) eluent. Methanol/water (49/11), UV detector: 220 nm, flow rate 0.6 ml/min, RT: 13.4 min, SESAS was also found to contain, squamocin G (2) asimicin/squamocin/H (3), 4-deoxyasimicin/squamocin/M, desacetyluvaricin/squamocin-L (5), motrilin/annonin-II/squamocin-C (6), neoannonin/squamocin/J (7), squamocin-K (8), squamocin-B (9), squamostatin-A (10), bullatalicin/squamostatin-B (11). Bullatanocin/squamostatin-C/annonin-IV/cherimolin-II (12) and the related unidentified compounds with retention times at 5.88 min, 14.18 min and 45.25 min in HPLC (FIG. 5).

Column Chromatography on Silicagel:

The silicagel column is prepared by stirring silicagel (400 g) with ethyl acetate and transferred into the glass column (10 g) of the extract obtained in example-I applied on to the silicagel column. Elution is carried out with ethyl acetate followed by acetone and methanol and 41 fractions (250 ml each) were collected. The solvent was removed from these fractions and like fractions were combined based on their composition on thin layer chromatography (silicagel) resulting in ten combined fractions, fraction-1 (2.48 g), fraction-2 (1.16 g), fraction-3 (2.68 g), fraction-4 (0.60 g); fraction-5 (0.19 g), fraction-6 (0.44 g), fraction-7 (0.74 g), fraction-8 (0.08 mg), fraction-9 (0.20 g) and fraction-10 (0.24 g) These fractions were further purified on reverse phase semi-preparative HPLC $\mu$ Bondapack C-18 column (19 mm×150 mm) and the mobile phase is methanol/water(90:10); UV $\lambda$=220 nm; flow rate 3 ml/mt. The amounts of pure acetogenins isolated are in the range 10–200 mg.

The residual seed powder (9.35 kg) after extraction of methanol was stripped of the adhering solvents packed again into the glass column and percolated with petroleum ether (b.p.6–80° C.)/hexane (401.) continuously and the petroleum ether b.p. 60–80° C./hexane extract was concentrated at atmospheric pressure or under reduced pressure resulting in an oil (1.8 kg). The remaining powder of seeds of Annona squamosa after the extraction with hexane was stripped the solvent and it weighed 7.3 kg.

EXAMPLE 2

The seeds of Annona squamosa (200 g) were disintegrated in a multimill (Gannon Private Ltd. Bombay, India) to a coarse powder having particle size ranging from BSS-7 (0.2 mm) to BSS-72 (2.4 mm) and the powder was packed into a glass column. The column packed with the powder of seeds of Annona squamosa was then continuously extracted by percolation with methanol (1000 ml) at ambient temperature. The resulting extract (890 ml) was concentrated at atmospheric pressure or under reduced pressure and the concentrate (20-ml) was stirred with ethyl acetate (40 ml) and water (20 ml) in a stirred vessel (5-min). The lighter ethyl acetate phase and the heavier aqueous phase separated in a phase separator. The heavier aqueous phase was stirred (5 min) again with ethyl acetate (40 ml) and both the phases were separated in a phase separator. The lighter ethyl acetate phases were combined and the solvent was removed under reduced pressure or at atmospheric pressure resulting in a brown viscous oil (9.3 g), which contained 16.96% of isosquamocin, by HPLC analysis. It also contained all the other compounds viz., squamocin-G, asimicin, 4-deoxyasimicin, desacetyluvaricin, motrilin, neoannonin, squamocin-K, squamocin-B, squamostatin-A, bullatalicin, bullatanocin and the related unidentified compounds with retention times at 5.88 min, 14.18 min and 45.25 min. The above residue containing 16.96% of isosquamocin and related compounds was stirred with petroleum ether b.p. 60–80° C./hexane in a stirred vessel and the solvent was separated. Traces of the solvent present in the remaining residue were removed under reduced pressure resulting in a brown viscous mass containing 38.89% of isoannonin (2.789 g) and this also constitutes the standardized extract of the seeds of Annona squamosa (SESAS). Its analytical HPLC is similar to that of the corresponding sample obtained in example-1. This sample was subjected to column chromatography (silica gel) and HPLC ($\mu$ bondapack C-18 column) by the procedures described in example-I resulting in the isolation of isosquamocin, squamocin-G, asimicin, 4-deoxyasimicin, desacetyluvaricin, motrilin, neoannonin, squamocin-K, squamocin-B, squamostatin-A, bullatalicin, bullatanocin and related compounds with retention times at 5.88 min, 14.18 min and 45.28 min in analytical HPLC.

EXAMPLE 3

The seeds of Annona squamosa (10 kg) were disintegrated in a multimill (Gannon Private Ltd., Bombay, India) to a coarse powder having particle size ranging from BSS-7 (0.12 mm) to BSS-72 (2.4 mm) and the powder was packed into a glass column. The column containing the powder of seeds of Annona squamosa was then continuously extracted by percolation with ethanol (40 lit) at ambient temperature. The resulting extract (36 lit) was concentrated at atmospheric pressure or under reduced pressure and the concentrated (1.76 lit) was stirred twice, successively with an equal volume of petroleum ether b.p. 60–80° C./hexane in a stirred vessel, petroleum ether/hexane phases were separated in a phase separator, and concentrated resulting a semisolid (13.5 g). The heavier phase was stirred with ethyl acetate (1.6 l) for 15 minutes and water (0.8 l) in a stirred vessel. The lighter ethyl acetate and heavier aqueous phases were separated in phase separator. The heavier phase was stirred again with ethyl acetate (2.4 l) and both the ethyl acetate phases were combined and the solvent was removed at atmospheric pressure or under reduced pressure resulting in a brown semisolid which was designed as standardized extract of seeds of Annona squamosa (SESAS) (200 g) and it was found to contain 38.89% of isosquamocin by analytical HPLC using a reverse phase $C_{18}$ column ($\mu$ bond pack LC 18 (3.0×150 mm) eluent: Methanol/water (82:18), UV detector: 220 nm, flow rate 0.6 ml/min, RT: 13.4 min, SESAS was also found to contain, squamocin G(2) asimicin/squamocin/H (3), 4-deoxyasimicin/squamocin/M(4), desacetyluvaricin/squamocin-L(5), motrilin/annonin-II/squamocin-C(6), neoannonin/squamojin/J(7), squamocin-K (8), squamocin-B(9), squamostatin-A(10), bullatalicin/squamostatin-B(11). Bullatanocin/squamostatin-C/annonin-IV/cherimolin-II (12) and the related unidentified compounds with retention times at 5.88 min, 14.18 min and 45.25 min in HPLC.

Column Chromatography on Silicagel:

The silicagel column is prepared by stirring silicagel (400 g) with ethyl acetate and (10 g) of the extract obtained in example-1 applied on to the silicagel column. Elution is carried out with ethyl acetate followed by acetone and methanol and 41 fractions (250 ml each) were collected. The solvent was removed from these fractions and like fractions were combined based on their compositions on thin layer chromatography (silicagel) resulting in ten combined fractions, fraction-1 (2.48 g), fraction-2 (1.16 g), fraction-3 (2.68 g), fraction-4 (0.60 g); fraction-5 (0.19 g), fraction-6 (0.44 g), fraction-7 (0.74 g), fraction-8 (0.08 mg), fraction-9 (0.20 g) and fraction-10 (0.24 g). These fractions were further purified on reverse phase semipreparative HPLC μ BondapackC-18 column (19 mm×150 mm) and the mobile phase is methanol/water (90:10); UV: λ=220 nm; flow rate: 3 ml/mint. The amounts of the pure acetogenins isolated are in the range 10–200 mg.

The residual seed powder (9.35 kg) after extraction of ethanol was stripped of the adhering solvents packed again into the glass column and percolated with petroleum ether (b.p.6–80° C.)/hexane (40 lit) continuously and the petroleum ether b.p. 60–80° C./hexane extract was concentrated at atmospheric pressure or under reduced pressure resulting in oil (1.8 kg). The remaining powder of seeds of *Annona squamosa* after the extraction with hexane was stripped the solvent and it weighed 7.3 kg.

EXAMPLE 4

The seeds of *Annona squamosa* (200 g) were disintegrated in a multimill (Gannon Private Ltd. Bombay, India) to a coarse powder having particle size ranging from BSS-7 (0.2 mm) to BSS-72 (2.4 mm) and the powder was packed into a glass column. The column packed with the powder of seeds of *Annona squamosa* was then continuously extracted by percolation with ethanol (1000 ml) at ambient temperature. The resulting extract (890 ml) was concentrated at atmospheric pressure or under reduced pressure and the concentrate (20 ml) was stirred with ethyl acetate (40 ml) and water (20 ml) in a stirred vessel (5 min). The lighter ethyl acetate phase and the heavier aqueous phase separated in a phase separator. The heavier aqueous phase was stirred (5 min) again with ethyl acetate (40 ml) and both the phases were separated in a phase separator. The lighter ethyl acetate phases were combined and the solvent was removed under reduced pressure or at atmospheric pressure resulting in a brown viscous oil (9.28 g), which contained 16.50% of isosquamocin, by HPLC analysis (FIG. 5). It also contained all the other compounds viz., squamocin-G, asimicin, 4-deoxyasimicin, desacetyluvaricin, motrilin, neoannonin, squamocin-K, squamocin-B, squamostatin-A, bullatalicin, bullatanocin and the related unidentified compounds with retention times at 5.88 min, 14.18 min and 45.25 min. The above residue containing 16.50% of isosquamocin and related compounds was stirred with petroleum ether b.p. 60–80° C./hexane in a stirred vessel and the solvent was separated. Traces of the solvent present in the remaining residue were removed under reduced pressure resulting in a brown viscous mass containing 39.00% of isoannonin (2.72 g) and this also constitutes the standardized extract of the seeds of *Annona squamosa* (SESAS). Its analytical HPLC is similar to that of the corresponding sample obtained in example-1. This sample was subjected to column chromatography (si gel) and HPLC (μ bondapack C-18 column) by the procedures described in example-1 resulting in the isolation of isosquamocin, squamocicin-G, asimicin, 4-deoxyasimicin, desacetyl uvaricin, motrilin, neoannonin, squamocin-K, squamocin-B, squamostatin-A, bullatalicin, bullatanocin and related compounds with retention times at 5.88 min, 14.18 min and 45.28 min in analytical HPLC.

EXAMPLE 5

The seeds of *Annona squamosa* (200 g) were disintegrated in a multimill (Gannon Private Ltd. Bombay, India) to a coarse powder having particle size ranging from BSS-7 (0.2 mm) to BSS-72 (2.4 mm) and the powder was packed into a glass column. The column packed with the powder of seeds of *Annona squamosa* was then continuously extracted by percolation with methanol water (80/20) at ambient temperature. The resulting extract (890 ml) was concentrated at atmospheric pressure or under reduced pressure and the concentrate (20 ml) was stirred with ethyl acetate (40 ml) in a stirred vessel (5 min). The lighter ethyl acetate phase and the heavier aqueous phase separated in a phase separator. The heavier aqueous phase was stirred (5 min) again with ethyl acetate (40 ml) and both the phases were separated in a phase separator. The lighter ethyl acetate phases were combined and the solvent was removed under reduced pressure or at atmospheric pressure resulting in a brown viscous oil (9.20 g), which contained 16.96% of isosquamocin, by HPLC analysis (FIG. 5). It also contained all the other compounds viz. squamocin-G, asimicin, 4-deoxyasimicin, desacetyluvaricin, motrilin, neoannonin, squamocin-K, squamocin-B, squamostatin-A, bullatalicin, bullatanocin and the related unidentified compounds with retention times at 5.88 min, 14.18 min and 45.25 min. The above residue containing 16.96% of isosquamocin and related compounds was stirred with petroleum ether b.p. 60–80° C./hexane in a stirred vessel and the solvent was separated. Traces of the solvent present in the remaining residue were removed under reduced pressure resulting in a brown viscous mass containing 38.76% of isoannonin (2.68 g) and this also constitutes the standardized extract of the seeds of *Annona squamosa*. Its analytical HPLC is similar to that of the corresponding sample obtained in example-1. This sample was subjected to column chromatography (si gel) and HPLC (μ bondapack C-18 column) by the procedures described in example-1 resulting in the isolation of isosquamocin, squamocicin-G, asimicin, 4-deoxyasimicin, desacetyluvaricin, motrilin, neoannonin, squamocin-K, squamocin-B, squamostatin-A, bullatalicin, bullatanocin and related compounds with retention times at 5.88 min, 14.18 min and 45.28 min in analytical HPLC.

EXAMPLE 6

The seeds of *Annona squamosa* (200 g) were disintegrated in a multimill (Gannon Private Ltd., Bombay, India) to a coarse powder having a particle size ranging from BSS-7 (0.2 mm) to BSS-72 (2.4 mm) and the powder was packed in a glass column. The column containing the powder of the seeds of *Annona squamosa* was continuously extracted with methanol/water (80/20) by percolation at ambient temperature. The resulting extract (890-ml) was concentrated at atmospheric pressure or under reduced pressure and the concentrate (20 ml) was stirred twice successively with an equal volume of petroleum ether b.p. 60–80° C./hexane in a stirred vessel, petroleum ether/hexane phases were separated in a phase separator and concentrated resulting in a semisolid. The heavier phase was stirred with ethyl acetate (40 ml) in a stirred vessel. The lighter ethyl acetate and heavier aqueous phases were separated in a phase separator. The heavier phase was stirred again with ethyl acetate (40 ml) and both the phases were separated in a phase separator. Both the ethyl acetate phases were combined and the solvent was removed at atmospheric pressure or under reduced pressure resulting in a brown semisolid which was designated standardized extract of seeds of *Annona squamosa* (2.98 g) and it was found to contain 25% of isosquqamocin by analytical HPLC using a reverse phases $C_{18}$ column as described in exmaple-1. It was also found to contain squamocin-G, asimicin, 4-deoxyasimicin, desacetyluvaricin, motrilin, neoannonin, squamocin-B squamocin-K, squamostatin-A, bullatalicin, bullatanocin and related unidentified compounds with retention times at 5.88 min, 14.18 min and 45.25 min in HPLC (FIG. 5).

EXAMPLE 7

The seeds of *Annona squamosa* (200 g) were disintegrated in a multimill (Gannon Private Ltd., Bombay, India) to a coarse powder having a particle size ranging from BSS-7 (0.2 mm) to BSS-72 (2.4 mm) and the powder was packed in a glass column. The column containing the powder of the seeds of *Annona squamosa* was continuously extracted with ethanol/water (80/20) by percolation at ambient temperature. The resulting extract (890-ml) was concentrated at atmospheric pressure or under reduced pressure and the concentrate (20-ml) was stirred twice successively with an equal volume of petroleum ether b.p. 60–80° C./hexane in a stirred vessel, petroleum ether/hexane phases were separated in a phase separator and concentrated resulting in a semisolid. The heavier phase was stirred with ethyl acetate (40 ml) in a stirred vessel. The lighter ethyl acetate and heavier aqueous phases were separated in a phase separator. The heavier phase was stirred again with ethyl acetate (40 ml) and both the phases were separated in a phase separator. Both the ethyl acetate phases were combined and the solvent was removed at atmospheric pressure or under reduced pressure resulting in a brown semisolid which was designated standardized extract of seeds of *Annona squamosa* (3.0 g) and it was found to contain 29% of isosquamocin by analytical HPLC using a reverse phases $C_{18}$ column as described in exmaple-1. It was also found to contain squamocin-G, asimicin, 4-deoxyasimicin, desacetyluvaricin, motrilin, neoannonin, squamocin-B squamocin-K, squamostatin-A, bullatalicin, bullatanocin and related unidentified compounds with retention times at 5.88 min, 14.18 min and 45.25 min in HPLC (FIG. 5)

EXAMPLE 8

The seeds of *Annona squamosa* (200 g) were disintegrated in a multimill (Gannon Private Ltd., Bombay, India) to a coarse powder having a particle size ranging from BSS-7 (0.2 mm) to BSS-72 (2.4 mm) and the powder was packed in a glass column. The column containing the powder of the seeds of *Annona squamosa* was continuously extracted with ethanol/water (8/2) by percolation at ambient temperature. The resulting extract (890 ml) was concentrated at atmospheric pressure or under reduced pressure and the concentrate (20 ml) was stirred with ethyl acetate (40 ml) in a stirred vessel. The lighter ethyl acetate and heavier aqueous phases were separated in a phase separator. The heavier phase was stirred again with ethyl acetate (40 ml) and both the phases were separated in a phase separator. Both the ethyl acetate phases were combined and the solvent was removed at atmospheric pressure or under reduced pressure resulting in a brown semi-solid which was designated standardized extract of seeds of *Annona squamosa* (2.95 g) and it was found to contain 30% of isosquamocin by analytical HPLC using a reverse phases $C_{18}$ column as described in exmaple-1. It was also found to contain squamocin-G, asimicin, 4-deoxyasimicin, desacetyl uvaricin, motrilin, neoannonin, sqamocin-B squamocin-K, squamostatin-A, bullatalicin, bullatanocin and related unidentified compounds with retention times at 5.88 min, 14.18 min and 45.25 min in HPLC (FIG. 5).

EXAMPLE 9

The seeds of *Annona squamosa* were disintegrated in a multimill (Gannon Private Ltd., Bombay, India) to a coarse powder having particle size ranging from BSS-7 (0.2 mm) to BSS-72 (2.4 mm) and the powder (100 g) was packed into a glass column. The column containing the powder of seeds of *Annon squamosa* was continuously extracted by percolation in separate columns with the following solvents (500 ml) viz., ethyl acetate chloroform, dichlormethane, 1,2-dichloroethane, diethyl ether, diisopropyl ether, methyl tertiary butyl ether, benzene, toluene, acetone, 2-butanone, propanol, n-butanol and acetonitrile at ambient temperature. The resulting extract (410 ml) was concentrated under atmospheric pressure or reduced pressure and the concentrate was stirred with petroleum ether b.p. 60–80° C./hexane (60 ml). The supernatant liquid was decanted and the remaining residue was stripped of traces of solvents at atmospheric pressure or under reduced pressure resulting in a pale yellow oil, which constitutes the standardized extract of the seeds of *Annona squamosa* (SESAS). The isosquamocin content and the yield of the product are given in parenthesis for each of these solvents is as follows by this procedure ethanol (0.84 g, 36.87%), ethyl acetate (0.95 g, 43.80%), chloroform (0.92, 28.59%), dichloromethane (1.49, 32.76%), 1,2-dichloroethane (0.64 g, 32.46%), diethyl ether (0.64 g, 51.07%), methyl tertiary butyl ether (0.76 g, 41.20), diisopropyl ether (1.02 g, 55.98%), benzene (0.93 g, 57.21%), toluene (1.21 g, 38.61%), acetone (1.30 g, 49.11%), 2-butanone (0.76 g, 43.96%), n-propanol (0.93 g, 44.94%), isopropanol (0.82 g, 37.16%), n-butanol (0.87 g, 36.61%) and acetonitrile (0.71 g, 53.81%). The isosquamocin content was estimated by HPLC as described in example-1. The HPLC of the standardized extract of the seeds of *Annona squamosa* obtained by using all the solvents mentioned above were similar and contained squamocin-G, asimicin, 4-deoxyasimicin, desacetyluvaricin, motrilin, neoannonin, squamocin-B, squamocin-K, squamostatin-A, bullatalicin, bullatanocin and the related unidentified compounds with retention times at 5.88 min, 14.18 min and 45.25 min in HPLC (FIG. 5).

EXAMPLE 10

The seeds of *Annona squamosa* were disintegrated in a multimill to a coarse powder having a mesh size in the range BSS-7 (0.12 mm) to BSS-72 (2.4 mm). The powder (1-kg) was subjected to extraction with petroleum ether (bp. 60–80° C./hexane) (14 h) and methanol (14 h) successively, in a sohxelet extraction apparatus. The supernatant petroleum ether/hexane soluble portion and the viscous mass (6.69 g) separated at the bottom of the extracting flask of the petroleum ether (B.P. 60–80° C./hexane) extraction were separated. The solvent from supernatant of the petroleum ether (BP. 60–80° C./hexane was removed at atmospheric pressure or under reduced pressure resulting in an oil (2.09 g).

The methanol extract was concentrated at atmospheric pressure or under reduced pressure and the concentrate (350 ml) was stirred with petroleum ether, b.p. 60–80° C./hexane five times successively in a stirred vessel and both the phases were separated. The lighter petroleum ether b.p. 60–80° C./hexane phases were combined and the solvent was stripped off resulting in an oil (58 g).

The heavier methanol phases was stirred twice with dichloromethane (100 ml) successively and the dichloromethane phases were combined and the solvent was removed at atmospheric pressure or under reduced pressure resulting in a viscous mass (6.3 g).

The above solid (6 g) was dissolved in ethyl acetate and subjected to column chromatography (sigel Acme less than 0.08 mm AC ME, Bombay, 200 g column was prepared by transferring a slurry of slicagel in ethyl acetate to a glass column) using ethyl acetate as an eluent. 41 fractions (100 ml) were collected. Fraction (2), Fractions (3–6), (7,12), (13–22), (23–44) and (45) yielded an unidentified compound (69 mg) enriched squamocin-G (1.028 g), enriched isosquamocin (1.613 g) enriched bullatalicin (0.60 g), enriched squamostatin (0.796 g) and an unidentified compound (0.842 g) respectively.

EXAMPLE 11

The standardized extract of seeds of *Annona squamosa* containing 30% isosquamocin (SESAS) was stirred with cyclohexannone (70 g) and emulsifier (creslox 3409, 10 g) in a stirred vessel and the resulting brown solution contained 6% of isosquamocin.

EXAMPLE 12

Standardized extract of seeds of *Annona squamosa* containing 30% isosquamocin (2 kg) was stirred with cyclohexanone (6.75 kg) the emulsifier (creslox 3409, 1 kg) and piperonyl butoxide (250 g) in a stirred vessel until a homogeneous solution was obtained and it contained 6% of isosquamocin.

EXAMPLE 13

Standardized extract containing 30% isosquamocin (20 g), cyclohexanone (44.5 g) solvent C-IX (20 g) emulsifier (creslox, 3409, 10 g) piperonyl butoxide (5 g) and epichlorohydrin (0.5 g) were stirred together in a stirred vessel until homogeneous solution was obtained and it contained 6% of isoquqmocin.

EXAMPLE 14

Standardized extract of seeds of *Annona squamosa* (20 g) containing 30% isosquamocin, solvent C-IX (65 g) and emulsifier (creslox 3433, 10 g) and piperonyl butoxide (5 g) were stirred together in a stirred vessel until a brown homogeneous solution was obtained and it contained 6% isosquamocin.

EXAMPLE 15

Chromic larveal growth bioassay % of control given in parenthesis. Larval growth and larval survival of standardized extract of seeds of *Annona squamosa* (SESAS) (25%, 85%) and some of its components squamocin-G (34%, 45%) isosquamocin (20%, 55%), bullatalicin (135%, 100%) and squamostatin-A (138%, 100%) at a concentration of 20 ppm were determined against newly hatched variegated cutworm (peridroma saucia, Noctuidae (n=20) for 10 days at 26° C. The EC 50 and LC 50 squamocin-G were found to be 5.65 ppm and 12 ppm respectively. Standardized extract of seeds of *Annona squamosa* (SESAS) was also found to cause 50% mortality of black wire weevils (otiorhydnchus sulcatus of 0.5% (1 ul dose). These bioassays were carried out according to the procedure described earlier (M. B. Isman, O. Koul, A. Luczynski and J. Kaminski, J. Agric. Food Chem. 38, 1406 (1990). These tests were performed by Prof. M. B. Isman and colleagues at University of British Columbia, Vancouver, Canada.

EXAMPLE 16

Insect antifeedant bioassay of squamocin-G and isosquamocin were found to be toxic to the first and third instar larvae of origental armyworm (*Mythimna separata* WLK) at a concentration of 10.05% (MeOH) at 27° causing 70% mortality compared to 7% mortality of untreated control. The sample solutions (10 $\mu$l of a 0.05% solution) were applied evenly to the lower surface of leaf discs (5 cm$^2$) cut from sorghum hybrid variety CSH5 and the discs were allowed to dry on filter papers. After drying the leaf, discs were offered to 10 first instar *M. separata* larvae in plastic cups or to one third instar larva in 9-cm (diameter) plastic petric dishes. All larvae were starved for 2 h before the test and the leaf and the leaf discs were kept on moisture filter papers to keep them turgid. The larvae were confined to leaf discs for 24 h and during the period the larvae scratched or consumed >80% of the leaf disc area in the untreated controls. The leaf discs were rated visually for the extent of feeding on a scale upto 1 to 9 (1=<10%, 2=11 to 20%, 3=21 to 30%, 4=31 to 40%, 5=41 to 7=61 to 70%, 8=71 to 80%, 9=>80% leaf area scratched consumed). The larvae were then stirred for 12 h and weighed. Isosquamocin was evaluated by this procedure and the results have shown that it drastically. The feeding of the leaves of sorghum hybrid variety CSH 5 at a concentration of 0.05% in methanol) in comparison with control (methanol) against the first instar and third instar larvae of oriental armyworm (*Mythimna separata* WLK). It is very toxic to first instar larvae causing high larval mortality and the results are presented below:

| | First instar larvae | | | Third instar larvae | |
|---|---|---|---|---|---|
| Treatment | Larval Survival (%) | Mean larval mass (mg) | Damage rating | Mean larval mass (mg) | Damage rating |
| isosquamocin | 10.4 | 0.2 | 1.3 | 15.7 | 1.0 |
| Control-Methanol | 93.3 | 9.7 | 8.3 | 31.1 | 8.0 |
| Control-untreated | 96.7 | 12.0 | 8.7 | 31.3 | 9.0 |
| S.E | 4.1 | 3.3 | 0.41 | 2.18 | 0.61 |

Dr. H. C. Sharma and his colleagues at ICRISAT, Patancherru, Andhra Pradesh performed these tests.

EXAMPLE 17

Squamocin-G and isosquamocin have also been found to be toxic to the insect pests at concentration of 250 ppm to Southern Corn rootworm (SCRW). Two spotted spidermite, green peach aphid (GPA) and corn plant hopper (GPH) when they were subjected evaluation screen (Eval) and evaluation screen delayed toxicity test EVDT for the insecticidal activity and results are summarized below:

| Compound | Type test | SCRW | TSSM | GPA | CP-H |
|---|---|---|---|---|---|
| Squamocin-G | EVAL | 100 | L8 | | |
| | EVADT | | L9 | L8 | G8 |
| Isoquamocin | EVAL | 100 | L8 | | |
| | EVADT | | L9 | | G8 |

L8 = Less than 80% mortality
L9 = Less than 90% reduction in population
G8 = Greater than 80% reduction in population

TABLE 1

Difference between the invention of the application and prior art

| U.S. Pat. No. 4,689,232 | Sahai et al. Chem. Pharm. Bull. 42, 1163 1994 | Fujimoto et al. | Born et al Planta Medica 56, 312, 1990 | Lobo, Balanagar Luro Island | K. Kawaza et al. Agri. Biol. Chem. 53, 2719, 1989 |
|---|---|---|---|---|---|
| Ground seeds extraction with hexane-extract discarded | Ground seeds soxlet extraction with Pet. Ether-allowed to stand 24 hours | Ground seeds Pet. Ether extraction | Pullvarized seeds extracted with ligroin | Ground seeds extracted with Methanol (Mesh) | Ground seeds extracted with a) hexane and b) ethylacetate successively |
| Residual powder extracted with water immiscible solvents | Supernatant decanted oily residue washed with Pet. Ether | Pet. Ether extract concentrate | Concentrated ligroin extract partitioned with Mesh/H$_2$ (95:5) | Mesh extract concentrated | Ethyl acetate concentrate partitioned with 10% aqueous methanol and hexane |
| Concentrated extract-treated with organic solvents like aliphatic halogenohydrocarbon, aliphatic esters or ethers | Pet Ether washing-supernatant-partitioned with Mesh:H$_2$ (10:1) | Separation of waxy solid and the supernatant | Mesh phase treated with Pet. Ether and Phase separated | Partition of mesh extract concentrate between Pet. Ether and water to remove polar constituents | The active aqueous methanol layer concentrated-subjected for column chromatography |
| Organic layer concentrated | Methanol (Mesh) Layer digested with ethyl acetate | Washing the semisolid with Pet. Ether | Pet. Ether phase concentrated-subjected for column chromatography using CHCl$_3$-Mesh | Pet. Ether extract column chromatography and HPLL | |
| Column chromatography using CHCl$_3$ | Ethyl acetate layer concentrated-subjected to column chromatography using CHCl$_3$—E$_{10}$Ac | Waxy solid-subjected to column chromatography CHCl$_3$-Mesh | Reverse phase HPLI | | |
| Reverse phase IIPLC | Subjecting to HPLL | | | | |

Example embodiments of the present invention have now been described in accordance with the above advantages. It will be appreciated that these examples are merely illustrative of the invention. Many variations and modifications will be apparent to those skilled in the art.

What is claimed is:

1. A process for the preparation of an extract of seeds of *Annona squamosa* comprising Isosquanmocin, said process comprising:

(a) disintegrating the *Annona squamosa* seeds into powder, (b) subjecting the powder of step (a) to continuous extraction with methanol or aqueous methanol, or ethanol or aqueous ethanol at an ambient temperature, (c) concentrating the extract of step (b) and stirring the concentrate with petroleum ether or hexane having boiling point in the range of 60–80° C. and phasing the stirred concentrate into a heavy phase and a light phase, (d) stirring the heavy phase of step (c) containing the active ingredient Isosquamocin, and optionally Squamocin-G, Squamocin-H, squamocin-M, Squamocin-L, Squamocin-C, Squamocin-J, Squamocin-K, Squamocin-B, Squamostatin-A, Squamostatin-B, Squamostatin-C or compounds derived from the plant *Annona squamosa* and having retention times of 5.88 minutes, 14.18 minutes, and 54.25 minutes in HPLC with suitable proportion of organic solvent and water into a mixture containing an organic phase and separating the organic phase, (e) concentrating the organic phase of step (d) to yield extract of *Annona squamosa* in the form of brown semisolid, (f) dissolving the semisolid from step (e) in an organic solvent and subjecting it to column chromatography over silica gel using eluants of increasing polarity to obtain a solid residue, and (g) dissolving the residue obtained from (f) and purifying the dissolved residue with methanol and water.

2. The process of claim 1, wherein in step (a), the disintegration of the seeds is carried out in a mill.

3. The process of claim 1, wherein in step (b), the particle size of the disintegrated seed powder obtained is 0.2–2.4 mm.

4. The process of claim 1, wherein in step (d) the organic solvent is selected from benzene, 2-butanone, chloroform, dichloromethane, dichloroethane, diethyl ether, disopropyl ether, ethyl acetate, MTB, and toluene.

5. The process of claim 1, wherein the organic solvent in step (d) is ethyl acetate and wherein step (e) comprises concentrating an ethyl acetate extract at atmospheric pressure or under reduced pressure.

6. The process of claim 1, wherein in step (e), the concentrated extract contains up to 57% of acetogenin.

7. The process of claim 1, wherein step (f) comprises dissolving the semisolid in solvent and purifying the dissolved semisolid through column chromatography resulting in isolation of purified acetogenin.

8. A process for the preparation of an extract of seeds of *Annona squamosa*, said process comprising: disintegrating the seeds into powder, continuously percolating the powdered seeds using a solvent at an ambient temperature through a glass column in which the powdered seeds are packed, concentrating the extract and stirring the extract so obtained with petroleum ether; decanting and discarding the supematant liquid to obtain a semisolid; and drying the semisolid at atmospheric pressure or reduced pressure to obtain extract of the seeds of *Annona squamosa* having up to 57% of acetogenin comprising Isosquamocin.

9. The process of claim 8, wherein the solvent used is selected from the group consisting of benzene, dichloromethane, dichloroethane, chloroform, ethyl acetate, acetone, 2-butanone, methyl tertiary butyl ether, disopropyl ether, n-butanol, and acetonitrile.

10. The process of claim 8, wherein a concentrate containing up to 6% Isosquamocin is obtained by extracting seeds of *Annona squamosa* having up to 57% acetogenins.

11. The process of claim 10, wherein the organic solvent used is selected from aromax, 2-butanone, cyclohexanone, dimethyl formamide, dimethyl pthalate, dioctylpthalate, isobutanol, isobutyl methyl ketone, isopropanol, solvent C-IX, xylene, and suitable combinations thereof.

* * * * *